United States Patent [19]

Phillipps et al.

[11] 4,335,121
[45] Jun. 15, 1982

[54] ANDROSTANE CARBOTHIOATES

[75] Inventors: Gordon H. Phillipps, Wembley; Brian M. Bain, Chalfont St. Peter; Ian P. Steeples, Ruislip Manor; Christopher Williamson, Cobham, all of England

[73] Assignee: Glaxo Group Limited, London, England

[21] Appl. No.: 234,113

[22] Filed: Feb. 13, 1981

[30] Foreign Application Priority Data

Feb. 15, 1980 [GB] United Kingdom ................ 8005174

[51] Int. Cl.³ .......................... C07J 7/00; A61K 31/56
[52] U.S. Cl. ................................. 424/241; 260/397.1
[58] Field of Search ...................... /Steroids MS File; 260/397.1; 424/241

[56] References Cited

U.S. PATENT DOCUMENTS 3,636,010 1/1972 Basel et al. ................. 260/397.1
3,828,080 8/1974 Phillipps et al. ............. 260/397.1
4,093,721 6/1978 Phillipps et al. ............. 260/397.1
4,188,385 2/1980 Edwards .................... 260/397.1

Primary Examiner—Elbert L. Roberts
Attorney, Agent, or Firm—Bacon & Thomas

[57] ABSTRACT

Compounds of the formula

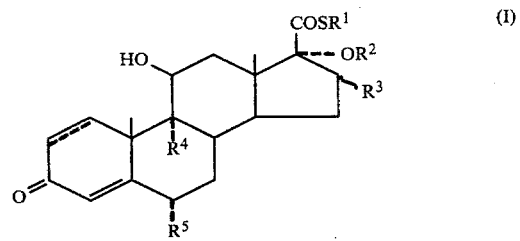

wherein $R^1$ represents a fluoro-, chloro- or bromomethyl group or a 2'-fluoroethyl group, $R^2$ represents a group $COR^6$ where $R^6$ is a $C_{1-3}$ alkyl group or $OR^2$ and $R^3$ together form a $16\alpha,17\alpha$-isopropylidenedioxy group; $R^3$ represents a hydrogen atom, a methyl group (which may be in either the $\alpha$- or $\beta$-configuration) or a methylene group; $R^4$ represents a hydrogen, chlorine or fluorine atom; $R^5$ represents a hydrogen or fluorine atom and symbol ⁓⁓⁓⁓⁓ represents a single or double bond have good anti-inflammatory activity, particularly on topical applications.

The compounds of formula I are prepared by esterification, halogenation, reduction, deprotection and reaction at a 9,11-double bond to form a 9α-halo-11β-hydroxy grouping.

Pharmaceutical compositions containing the compounds of formula I and methods for the use of the compounds are described and claimed.

25 Claims, No Drawings

ANDROSTANE CARBOTHIOATES

The present invention relates to anti-inflammatory steroids of the androstane series.

Anti-inflammatory steroids are most typically of the corticoid type, i.e. are pregnane derivatives. Our United Kingdom Pat. Nos. 1,384,372, 1,438,940 and 1,514,476 describe esters of certain androstane 17α-carboxylic acids having anti-inflammatory activity. European Patent Application No. 79300500.0 (Publication No. 0004741) describes esters of androstane 17β-carbothioic acids also possessing anti-inflammatory activity. We have now discovered that certain androstane compounds containing a haloalkyl carbothioate grouping in the 17β-position have particularly advantageous anti-inflammatory properties as discussed in greater detail below.

The new androstane compounds may be represented by the formula

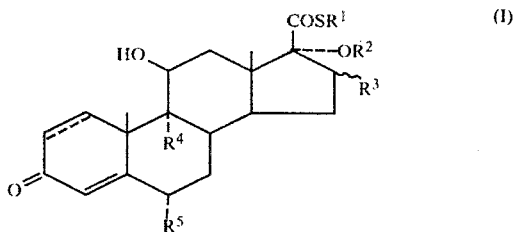

wherein $R^1$ represents a fluoro-, chloro- or bromo-methyl group or a 2′-fluoroethyl group; $R^2$ represents a group $COR^6$ where $R^6$ is a $C_{1-3}$ alkyl group or $OR^2$ and $R^3$ together form a 16α,17α-isopropylidenedioxy group; $R^3$ represents a hydrogen atom, a methyl group (which may be in either the α- or β- configuration) or a methylene group; $R^4$ represents a hydrogen, chlorine or fluorine atom; $R^5$ represents a hydrogen or fluorine atom and symbol ≈≈≈ represents a single or double bond.

The new compounds of formula (I) have good anti-inflammatory activity, particularly on topical application, as judged by the McKenzie patch test in man and as measured by the reduction of croton oil induced oedema when the compounds are applied topically to the skin of mice and rats.

Certain of the compounds show good topical anti-inflammatory activity in the croton oil ear test coupled with minimal hypothalamus-pituitary-adrenal-suppressive activity after topical application in the same animal species. These results indicate that such compounds may be of value in the local treatment of inflammation in man and animals with minimal liability to cause undesired systemic side effects.

Compounds of formula (I) which are preferred for their good anti-inflammatory activity include the following categories namely (a) those in which $R^1$ is chloro- or fluoromethyl (b) those in which $R^2$ is acetyl or propionyl, preferably propionyl, (c) those in which $R^4$ is fluorine (d) those in which $R^5$ is fluorine (e) the 1,4-dienes, and (f) those 1,4-dienes in which $R^4$ is fluorine and $R^3$ is hydrogen, α- and β-methyl or methylene.

Compounds of formula (I) which have good anti-inflammatory activity coupled with minimal hypothalamuspituitary-adrenal-suppressive activity when applied topically include 1,4-dienes in which $R^1$ is chloro- or fluoro-methyl, $R^4$ and $R^5$ are fluorine and in particular those in which $R^3$ is α-methyl.

Especially preferred compounds according to the invention in view of their good topical anti-inflammatory activity and favourable ratio of topical anti-inflammatory activity to undesired systemic activity include:

S-chloromethyl 9α-fluoro-11β-hydroxy-16α-methyl-3-oxo-17α-propionyloxyandrosta-1,4-diene-17β-carbothioate;

S-chloromethyl 9α-fluoro-11β-hydroxy-16-methylene-3-oxo-17α-propionyloxyandrosta-1,4-diene-17β-carbothioate;

S-fluoromethyl 6α,9α-difluoro-11β-hydroxy-16α,17α-isopropylidenedioxy-3-oxoandrosta-1,4-diene-17β-carbothioate;

S-fluoromethyl 6α,9α-difluoro-11β-hydroxy-16α-methyl-3-oxo-17α-propionyloxyandrosta-1,4-diene-17β-carbothioate;

S-chloromethyl 6α,9α-difluoro-11β-hydroxy-16α-methyl-3-oxo-17α-propionyloxyandrosta-1,4-diene-17β-carbothioate. The last compound is especially preferred in view of its particularly favourable ratio and in addition minimal skin atrophy.

The compounds of formula (I) may be prepared by a variety of different processes.

One such process comprises esterifying an androstane compound corresponding to formula (I) but containing either a free 17β-carbothioic acid group (or functionally equivalent group) or a free 17α-hydroxy group ($R^3$ being a hydrogen atom or a methyl or methylene group), any other reactive groups present in the molecule being suitably protected as desired.

For example, a salt of the parent 17β-carbothioic acid such as an alkali metal, e.g. lithium, sodium or potassium, salt or an alkylammonium, e.g. triethylammonium or tetrabutylammonium, salt may be reacted with an appropriate alkylating agent, preferably in a polar solvent such as a ketone, e.g. acetone or an amide such as dimethylformamide, dimethylacetamide or hexamethylphosphoramide, conveniently at a temperature of 15° to 100° C. The alkylating agent may comprise an appropriate dihalo compound i.e. one containing a further halogen atom (preferably a bromine or iodine atom) in addition to the halogen atom of the desired $R^1$ group. This process is particularly applicable to the preparation of compounds in which $R^1$ is a choromethyl group, the alkylating agent advantageously being bromochloromethane.

Alternatively, the parent 16-hydrogen, methyl or methylene-17α-hydroxy-17β-carbothioates corresponding to compounds of formula I may be subjected to esterification of the 17α-hydroxyl group. This may be effected by conventional techniques, e.g. by reacting the parent 17α-hydroxy compound with a mixed anhydride of the required carboxylic acid, which may, for example, be generated in situ by reacting the carboxylic acid with an appropriate anhydride such as trifluoroacetic anhydride, preferably in the presence of an acid catalyst, e.g. p-toluenesulphonic acid or sulphosalicylic acid. Alternatively, the mixed anhydried may be generated in situ by reaction of a symmetrical anhydride of the required acid with an appropriate further acid, e.g. trifluoroacetic acid.

The reaction is advantageously effected in an organic solvent medium such as benzene, methylene chloride or an excess of the carboxylic acid employed, the reaction being conveniently effected at a temperature of 20°–100° C.

Alternatively, the 17α-hydroxy group may be esterified by reaction of the parent 17α-hydroxy compound with the appropriate acid anhydried or acid chloride, if desired, in the presence of non-hydroxylic solvents, e.g. chloroform, methylene chloride or benzene, and preferably in the presence of a strong acid catalyst, e.g. perchloric acid, p-toluene sulphonic acid or a strongly acidic cation exchange resin, e.g. Amberlite IR 120, the reaction being conveniently effected at a temperature of 25° to 100° C.

The compounds of formula (I) may also be prepared by reacting a corresponding androstane compound containing a 17β-substituent of formula —COS(CH$_2$)$_n$Y (wherein Y represents a displaceable substituent and n is 1 or 2) with a compound serving to replace the group Y by a halogen atom.

Thus the compounds of formula (I) may be subjected to a halogen exchange reaction serving to replace the group Y where this is halogen by a different halogen substituent. Thus the bromomethyl, fluoromethyl and fluoroethyl 17β-carbothioate compounds may be prepared from the corresponding iodomethyl or bromoethyl 17β-carbothioate compounds using a bromide salt such as lithium bromide in the case of the bromomethyl 17β-carbothioate compounds or an appropriate fluoride e.g. silver monofluoride or silver difluoride in the case of the fluoromethyl or fluoroethyl 17β-carbothioate compounds. The starting iodomethyl 17β-carbothioate compounds may be prepared from the corresponding chloromethyl 17β-carbothioate compounds using for example, an alkali metal, alkaline earth metal or quaternary ammonium iodide e.g. sodium iodide.

The reaction is advantageously effected in a solvent medium comprising for example acetone, acetonitrile methyl eythyl ketone, dimethylformamide, dimethylacetamide or ethanol.

The foregoing reactions may also be carried out on starting materials having a variety of substituents or groupings which are subsequently converted into those substituents or groupings which are present in the compounds of the invention as defined above.

The 11β-hydroxy compounds of formula (I) may thus be prepared by reduction of a corresponding 11-oxo compound, e.g. using an alkali metal or alkaline earth metal borohydride, e.g. sodium or calcium borohydride, conveniently in an alcoholic or aqueous alcoholic solvent such as methanol or ethanol.

Such an 11-keto compound may be prepared by oxidation of a corresponding 11α-hydroxysteroid, for example using a chromic acid reagent such as Jones' reagent.

An 11β-hydroxy compound of formula (I) may also be obtained by deprotection of a corresponding compound having a protected hydroxyl group at the 11β-position, for example a tri C$_{1-6}$ alkylsilyloxy group such as the trimethylsilyloxy group or a perfluoro- or chloroalkanoyloxy group such as the trifluoroacetoxy group. Removal of the protecting group may be effected by hydrolysis, the trialkylsilyl group, being readily removed by mild acid or basic hydrolysis or particularly conveniently using fluoride e.g. hydrogen fluoride or an ammonium fluoride. The perfluoro- or chloro-alkanoyl protecting group may also be removed by mild acid or basic hydrolysis or alcoholysis, but preferably under acidic conditions when R$^4$ is a chlorine atom. Such a protected hydroxyl group may be introduced, for example, by reacting an 11β-hydroxy steroid with an appropriate reagent such as a trialkylsilyl halide or a perfluoro- or chloro-alkanoic anhydride.

Compounds of formula (I) may also be produced by reaction of a corresponding compound having a 9,11-double bond (and no substituent in the 11-position) with reagents serving to introduce the required 9α-halo-11β-hydroxy grouping. This may involve initial formation of a bromohydrin by reaction with an N-bromo-amide or -imide such as N-bromosuccinimide, followed by formation of the corresponding 9β,11β-epoxide by treatment with a base and reaction of the epoxide with hydrogen fluoride or hydrogen chloride to introduce the required fluorohydrin or chlorohydrin grouping respectively. Alternatively, the 9,11-olefin compound may be reacted with an N-chloro-amide or -imide to introduce the required 9α-chloro-11β-hydroxy grouping directly.

The Δ$^4$-compounds according to the invention can conveniently be prepared by partial reduction of the corresponding Δ$^{1,4}$-compound, for example, by hydrogenating using a palladium catalyst, conveniently in a solvent e.g. ethyl acetate or by homogeneous hydrogenation using for example tris(triphenylphosphine)rhodium chloride, conveniently in a solvent such as benzene, or by exchange hydrogenation using for example cyclohexene in the presence of a palladium catalyst in a solvent e.g. ethanol, preferably under reflux. This reduction may be carried out on a haloalkyl ester where this is sufficiently stable in such a reaction or may be effected at an earlier stage.

The above mentioned compounds containing a free —COSH group in the 17β-position may be prepared for example by aminolysis with rearrangement of a suitable 17β-thiocarbamoyloxycarbonyl androstane. The 17β-thiocarbamoyloxycarbonyl androstane is a mixed anhydride of the corresponding 17β-carboxylic acid and a thiocarbamic acid and is conveniently prepared by reaction of a salt of the 17β-carboxylic acid 17α-ester or 16α,17α-acetonide with a thiocarbamoyl halide. The thiocarbamoyl group is N,N-disubstituted, and may thus have the formula —COOCSNR$^A$R$^B$, where R$^A$ and R$^B$, which may be the same or different, are alkyl groups, e.g. C$_{1-4}$ alkyl groups or R$^A$ and R$^B$ together with the nitrogen atom to which they are attached form a 5–8 membered ring which may optionally contain an additional hetero atom selected from oxygen, nitrogen and sulphur and/or which may optionally be substituted by one or two C$_{1-3}$ alkyl e.g. methyl groups. Preferably R$^A$ and R$^B$ are C$_{1-4}$ alkyl substituents, the N,N-dimethylthiocarbamoyl group being preferred. The thiocarbamoyl halide is preferably the chloride. The reaction may be accelerated by the addition of an iodide salt e.g. sodium iodide.

The initial androstane 17β-carboxylate salt may be for example, an alkali metal, e.g. sodium or potassium, alkaline earth metal, e.g. calcium, salt or a salt of a tertiary amine, e.g. triethylamine.

Aminolysis with rearrangement may be carried out for example by heating the mixed anhydride to an elevated temperature e.g. in the presence of ammonia, a primary amine or more preferably a secondary amine such as diethylamine or pyrrolidine. In the starting 17β-carboxylic acids, the 16- and 17α-positions will conveniently be substituted by the —R$^3$ and —OR$^2$ groupings desired for the final product of formula (I).

17α-Hydroxy androstane compounds in the 16-methylene series which contain the desired 17β-carbothioic acid grouping, as described above, may be prepared from the corresponding 16β-methyl-16α,17α-epoxy 17β-thiocarboxylic acid, by effecting a rearrangement using a strong acid e.g. a strong carboxylic acid such as trifluoroacetic acid. These 16α,17α-epoxides may be prepared from the corresponding 17β-carboxylic acids by treatment with an onium salt of a 2-halo-azaaromatic compound, followed by treatment of the resulting product with hydrogen sulphide or a salt thereof to give the free 17β-carbothioic acid which may be alkylated as described above, preferably in situ to give the desired 17β-carbothioate group.

16α,17α-Isopropylidenedioxy compounds of formula (I) may similarly be prepared by treating a corresponding 17β-carboxylic acid with an onium salt of a 2-halo-azaaromatic compound followed by treatment of the resulting product with hydrogen sulphide to give the free 17β-carbothioic acid which may then be esterified as described above.

Onium salts of 2-halo-aza-aromatic compounds are capable of effecting carboxyl activation. Such reagents include 2-halo-N-alkyl- or 2-halo-N-phenyl-pyridinium or pyrimidinium salts carrying 1 to 2 further substituents selected from phenyl and lower (e.g. $C_{1-4}$) alkyl groups, such as methyl. The 2-halogen atoms can be fluorine, chlorine, bromine or iodine atoms. The salts are preferably sulphonates, e.g. tosylates; halides e.g. iodides; fluoroborates or perfluoroalkylsulphonates, a convenient salt being 2-fluoro-N-methylpyridinium tosylate or 2-chloro-N-methylbenzothiazolium trifluoromethanesulphonate.

The 16α,17α-epoxy-16β-methyl-17β-carboxylic acid compounds used as starting materials in the above process may be prepared in conventional manner, e.g. as described in British Patent Specification No. 1,517,278.

The starting materials employed in the process described herein for the preparation of compounds of formula (I) are new and constitute a further feature of the invention; they include compounds of the general formula (II)

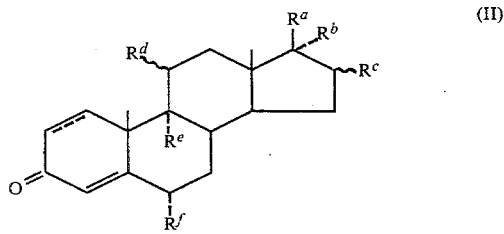

(wherein $R^a$ represents a thiocarbamoyloxycarbonyl group —COOCSNR$^A$R$^B$ where $R^A$ and $R^B$ are as defined above, or a group of the formula —COSR$^{1A}$, where $R^{1A}$ represents a hydrogen atom or is a group as defined above for $R^1$ or is a group convertible thereto and $R^b$ represents an esterified hydroxyl group or $R^b$ and $R^c$ together represent in isopropylidenedioxy group; or where $R^a$ represents a group COSR$^{1A}$, $R^b$ is optionally a hydroxyl group;

$R^c$ represents a hydrogen atom, a methyl group (which may be in either the α- or β-configuration) or a methylene group;

$R^d$ represents a hydroxy or protected hydroxy group (in either the α- or β-configuration) or an oxo group;

$R^e$ represents a hydrogen, bromine, chlorine or fluorine atom; or $R^d$ and $R^e$ together represent a carbon-carbon bond or an epoxy group in the β-configuration;

$R^f$ represents a hydrogen or a fluorine atom; and the symbol ═══ represents a single or double bond and salts of these compounds which have a free carbothioic acid group; with the exclusion of compounds of formula (I) as hereinbefore defined.

Where $R^d$ represents a protected hydroxyl group, this may, for example be a trialkylsilyloxy group or a perfluoro- or perchloro-alkanoyloxy group as defined previously.

The 17α-hydroxy 17β-carbothioic acids of formula (II) and salts thereof may be converted into the 17α-hydroxy 17β-carbothioates of formula (II) where $R^a$ represents the group COSR$^1$ as defined in formula (I) or into the 17β-carbothioic acid 17α-esters of formula (II) by the processes described above for preparing the compounds of formula (I). The esterification of the 17α-hydroxy group is preferably effected with the appropriate carboxylic acid chloride in a solvent such as a halogenated hydrocarbon e.g. dichloromethane, and advantageously in the presence of a base such as triethylamine, preferably at a low temperature e.g. 0° C.

The 17α-hydroxy 17β-carbothioic acids of formula (II) and salts thereof are thus particularly useful intermediates for preparing the androstane 17β-carbothioates of formula (I); those in which $R^c$ represents a hydrogen atom, an α- or β-methyl group or a methylene group, $R^e$ represents a hydrogen, chlorine or fluorine atom, $R^d$ represents a hydroxy group in the β-configuration or an oxo group being preferred. More preferred compounds and salts thereof include those compounds in which $R^c$ represents a methyl group in the α- or β-configuration or a methylene group; $R^e$ represents a fluorine atom, $R^d$ represents a hydroxy group in the β-configuration or an oxo group and the symbol ═══ in the 1,2 position represents a carbon-carbon double bond.

Especially preferred compounds of formula II thus include, for example, the following:

9α-fluoro-11β,17α-dihydroxy-16β-methyl-3-oxoandrosta-1,4-diene-17β-carbothioic acid; 9α-fluoro-11β,17α-dihydroxy-16α-methyl-3-oxoandrosta-1,4-diene-17β-carbothioic acid; 9α-fluoro-11β,17α-dihydroxy-16-methylene-3-oxoandrosta-1,4-diene-17β-carbothioic acid; 6α,9α-difluoro-11β,17α-dihydroxy-16α-methyl-3-oxoandrosta-1,4-diene-17β-carbothioic acid and the corresponding 11-ketones and salts thereof.

One advantage of the above intermediates is that they permit direct haloalkylation to give haloalkyl 17β-carbothioates when the corresponding thiols R$^1$SH are not available. The salts of these 17α-hydroxy 17β-carbothioic acids may, for example be alkali metal, e.g. lithium, sodium or potassium salts; alkaline earth metal, e.g. calcium or magnesium salts; tertiary amine salts, e.g. pyridinium or triethylammonium salts; or quaternary ammonium salts, e.g. tetrabutylammonium salts.

The 17α-hydroxy 17β-carbothioic acids may, for example, be prepared by reaction of a reactive derivative of a corresponding 17α-hydroxy-17β-carboxylic acid with hydrogen sulphide or a sulphide or hydrosulphide salt thereof. In general, the cation of the sulphide or hydrosulphide salt may be for example an alkali metal salt such as sodium or potassium hydrogen sulphide. The above-mentioned reactive derivatives correspond to compounds of formula (II) where $R^b$ is a hydroxyl group and the group —COR$^7$ is present at the 17β-position wherein $R^7$ represents a group of the formula

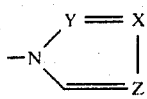

in which X, Y and Z, which may be the same or different, each represent CH or N, one or two of X, Y and Z being N, the heterocyclic ring optionally being substituted on at least one carbon atom by a lower alkyl group (e.g. with 1 to 4 carbon atoms, such as a methyl group) and/or where the heterocyclic ring contains two adjacent carbon atoms, the said ring optionally carrying a benzene ring fused to the said adjacent carbon atoms.

The reactive derivatives of formula (III) are preferably prepared by reacting corresponding 17α-hydroxy 17β-carboxylic acids of formula (II) with a symetric or asymmetric compound of the formula:

$$R^7—W—R^7 \qquad (IV)$$

wherein W represents the group CO, CS, SO or $SO_2$ and the groups $R^7$, which may be the same or different, have the above meanings.

The compounds of formula (III) are conveniently symmetric. In general, compounds of formula (III) in which W represents CO, CS or SO will be used. Thus, for example, especially useful compounds include N,N'-carbonyldi(1,2,4-triazole), N,N'-carbonyldibenzotriazole, N,N'-carbonyldibenzimidazole, N,N'-carbonyldi(3,5-dimethylpyrazole), N,N'-thionyldiimidazole and especially N,N'-carbonyldiimidazole and N,N'-thiocarbonyldiimidazole.

The preparation of a 17α-hydroxy 17β-carbothioic acid having the formula (II) as herein defined is conveniently effected by reaction of a 17α-hydroxy 17β-carboxylic acid with a compound of formula (III) followed by reaction of the intermediate product having the 17β—$COR^7$ grouping with hydrogen sulphide or a salt thereof preferably in situ without isolation of the intermediate.

The 17α-acyloxy 17β-carbothioic acid of formula II may be obtained in a similar manner directly from the corresponding 17α-acyloxy 17β-carboxylic acid by reaction with a compound of formula (III). The 17α-acyloxy 17β-carboxylic acids may be prepared by esterification of the corresponding 17α-acyloxy 17β-carboxylic acids by the methods described in BP No. 1,384,372.

The reaction with the compound of formula (III) is conveniently effected in the presence of an inert anhydrous solvent e.g. a substituted amide solvent such as N,N-dimethylformamide or N,N-dimethylacetamide, desirably in the absence of water, advantageously at or below ambient temperature e.g. at a temperature of from $-30°$ C. to $+30°$ C. The reaction is conveniently effected under approximately neutral conditions, advantageously in an inert atmosphere, e.g. under nitrogen. The same solvents and conditions are also applicable to the subsequent reaction with $H_2S$ or a salt thereof. The heterocyclic compound e.g. imidazole or 1,2,4-triazole formed as a by-product may, for example, be readily removed by extraction with water.

The foregoing reactions may also be carried out on compounds having a variety of substituents or groupings which are subsequently converted as described previously to compounds of formula (I).

The androstane 17β-carboxylic acid starting materials employed in the above processes may be prepared in conventional manner, e.g. by oxidation of an appropriate 21-hydroxy-20-keto pregnane for example with periodic acid, in a solvent medium and preferably at room temperature. Alternatively, sodium bismuthate may be employed to effect the desired oxidative removal of the 21-carbon atom of a 17α-acyloxy pregnane compound. As will be appreciated should the starting pregnane compound contain any substituent sensitive to the above desired oxidation, such a group should be suitably protected.

The following examples illustrate the invention.

Melting points were determined in °C. on a Kofler block and are uncorrected. Optical rotations were determined at room temperature on solutions in dioxan.

T.l.c. (Thin layer chromatography), p.l.c. (Preparative layer chromatography) and h.p.l.c. (High performance liquid chromatography) were carried out over silica.

Solutions were dried over magnesium sulphate unless stated otherwise.

PREPARATION I

9α-Fluoro-11β-hydroxy-16β-methyl-3-oxo-17α-propionyloxyandrosta-1,4-diene-17β-carbothioic acid (I)

A solution of 9α-fluoro-11β-hydroxy-16β-methyl-3-oxo-17α-propionyloxyandrosta-1,4-diene-17β-carboxylic acid (5.00 g) solvated with ethyl acetate (½ mole) and triethylamine (5.3 ml) in dichloromethane (75 ml) was stirred under nitrogen and treated with dimethylthiocarbamoyl chloride (5.071 g). After 24 h more reagent (5.320 g) was added. After 47 h the mixture was diluted with ethyl acetate and washed with N-hydrochloric acid, 5% sodium bicarbonate solution and water, dried and evaporated to give a viscous yellow oil (9.043 g). This was dissolved in diethylamine (50 ml) then stirred and heated at reflux under nitrogen for 5.75 h. The resulting brown solution was added to a mixture of concentrated hydrochloric acid (50 ml), water (250 ml) and ethyl acetate (50 ml). The products were further extracted with ethyl acetate, then the acid products were back-extracted into 5% sodium carbonate solution. The acqueous phase was acidified with 6 N-hydrochloric acid (50 ml) and extracted with ethyl acetate. The extracts were washed with N-hydrochloric acid and water, dried and evaporated to a buff solid (3.440 g). This was recrystallised from acetone to give pale buff crystals (1.980 g) of the title 17β-carbothioic acid, m.p. 172°–173°.

The analytical sample was obtained after two recrystallizations from acetone as white crystals, m.p. 177°–179°, $[\alpha]_D+110°$ (c 1.05).

PREPARATION II

S-Chloromethyl 9α-fluoro-16β-methyl-3,11-dioxo-17α-propionyloxyandrosta-1,4-diene-17β-carbothioate (II)

8 N-Jones reagent (1.5 ml) was added dropwise over 10 mins to a stirred solution of the compound of Example 1 (hereinafter disclosed) (998 mg) in acetone (2 ml) and dimethylformamide (2 ml). After 30 mins the reaction mixture was slowly diluted with water (100 ml) with stirring, and the resulting suspension was refrigerated for 1 h. The precipitate was collected by filtration, washed with water and dried to give a cream coloured solid (877 mg). P.l.c. in chloroform-acetone (10:1) gave a white foam (755 mg) which was crystallised twice from acetone to give white needles of the title 11-ketone (523 mg) m.p. 204°–205°, $[\alpha]_D+94°$ (c 1.04).

PREPARATION III

17β N,N Dimethylthiocarbamoyloxycarbonyl-9α-fluoro-11β-hydroxy-16α-methyl-17α-propionyloxyandrosta-1,4-diene-3-one (III)

A solution of 9α-fluoro-11β-hydroxy-16α-methyl-3-oxo-17α-propionyloxyandrosta-1,4-diene-17β-carboxylic acid (0.434 g) in dichloromethane (8 ml) was treated successively with triethylamine (0.14 ml), dimethylthiocarbamoyl chloride (0.248 g), and sodium iodide (0.149 g) and the mixture was stirred under nitrogen at 20° C. for 6 h. Ethyl acetate (30 ml) was added and the total volume was reduced by half in vacuo. Further ethyl acetate (50 ml) was added and the solution was washed with water, 2 N-hydrochloric acid, water, 3% sodium hydrogen carbonate, water and saturated sodium chloride solution then dried. The solution was concentrated in vacuo when the product crystallised (0.329 g). This was recrystallised from acetone (2×) to give the title anhydride as white needles, m.p. 191°–193°, $[\alpha]_D+82°$ (c 0.57).

PREPARATION IV

9α-Fluoro-11β-hydroxy-16α-methyl-3-oxo-17α-propionyloxyandrosta-1,4-diene-17β-carbothioic acid (IV)

A stirred suspension of (III) (2.467 g) in diethylamine (25 ml) was heated at reflux under nitrogen. After 3.5 h. the reaction was poured into iced 3 N hydrochloric acid (300 ml) and the mixture was extracted with ethyl acetate. The combined extracts were washed with water and were extracted with 5% sodium carbonate solution. The combined aqueous extracts were washed with ethyl acetate, then covered with ethyl acetate and acidified with hydrochloric acid to pH 1. The aqueous phase was extracted with further ethyl acetate and the combined extracts were washed with water, saturated sodium chloride solution, dried and the solvent was removed in vacuo. The residue was crystallised twice from acetone to give the title carbothioic acid as white needles (1.309 g) m.p. 141°–143°, $[\alpha]_D+30°$ (c 0.51).

PREPARATION V

11β-Hydroxy-3-oxo-17α-propionyloxyandrosta-1,4-diene-17β-carboxylic acid (V)

A solution of 11β,17α-dihydroxy-3-oxoandrosta-1,4-diene-17β-carboxylic acid (13.5 g), and triethylamine (18 ml) in dichloromethane (500 ml) was cooled to 4° C. and treated portionwise during 15 minutes with propionyl chloride (14.2 ml). Stirring was continued at 4° C. for a total time of 1 h and the mixture was washed successively with 3% sodium hydrogen carbonate, water, 2 N-hydrochloric acid, water and saturated brine, then dried and evaporated under reduced pressure. The residue was dissolved in acetone (300 ml) and diethylamine (14.3 ml) was added with stirring. After 1 h at 20° C. the solvent was removed under reduced pressure, and the residue was dissolved in water (150 ml). After acidification to pH 1 with 2 N-hydrochloric acid the product was extracted with ethyl acetate. The combined extracts were washed with water and saturated brine, dried and then concentrated to a low volume. The solid product was collected by filtration, washed with ethyl acetate and dried in vacuo at 50° to give the title 17α-propionate carboxylic acid as crystals (13.309 g), $[\alpha]_D+2°$ (c 1.10,). A portion (389 mg) was recrystallised twice from methanol to give an analytical sample (256 mg) m.p. 244°–245° (decomp), $[\alpha]_D+3°$ (c 0.83).

PREPARATION VI

6α,9α-Difluoro-11β-hydroxy-16α-methyl-3-oxo-17α-propionyloxyandrosta-1,4-diene-17β-carboxylic acid (VI)

A solution of 6α,9α-difluoro-11β,17α-dihydroxy-16α-methyl-3-oxoandrosta-1,4-diene-17β-carboxylic acid (2.113 g) and triethylamine (2.5 ml) in dichloromethane (60 ml) was stirred and treated at ca 0° C. with propionyl chloride (1.85 ml). After 1 h the mixture was diluted with more solvent (50 ml) and washed successively with 3% sodium hydrogen carbonate, water, 2 N-hydrochloric acid, water, saturated brine, then dried and evaporated to a buff solid. This was dissolved in acetone (50 ml) and diethylamine (2.5 ml) was added. After 1 h at 22° C. the solvent was removed in vacuo and the residual gum was dissolved in water (30 ml). Acidification to pH 1 with 2 N-hydrochloric acid precipitated a solid, which was collected, washed with water, and dried to give the title carboxylic acid 17α-propionate (2.230 g), m.p. 220°–225°, $[\alpha]_D+4°$ (c 0.70).

PREPARATION VII

17β-N,N-Dimethylthiocarbamoyloxycarbonyl-9α-fluoro-11β-hydroxy-16α,17α-isopropylidenedioxyandrosta-1,4-diene-3-one (VII)

A solution of 9α-fluoro-11β-hydroxy-16α,17α-isopropylidenedioxy-3-oxoandrosta-1,4-diene-17β-carboxylic acid (1.000 g) in dichloromethane (15 ml) and triethylamine (0.33 ml) under nitrogen was treated with N,N-dimethylthiocarbamoyl chloride (588 mg) and the mixture was stirred at room temperature. After 68 g the reaction mixture was diluted with ethyl acetate (50 ml) and washed with N-hydrochloric acid (2.10 ml), 5% sodium hydrogen carbonate solution and water, dried and evaporated to a pale yellow crystalline solid (1.123 g). P.l.c. of a portion (200 mg) in chloroformacetone (9:1) gave an off-white solid (161 mg) which crystallised from ethyl acetate as white needles of the title mixed anhydride (131 mg), m.p. 279°–281°, $[\alpha]_D+174°$ (c 0.61, dimethylsulphoxide).

PREPARATION VIII

17β-N,N-Dimethylthiocarbamoyloxycarbonyl-6α,9α-difluoro-11β-hydroxy-16α,17α-isopropylidenedioxyandrosta-1,4-diene-3-one (VIII)

A solution of 6α,9α-difluoro-11β-hydroxy-16α,17α-isopropylidenedioxy-3-oxoandrosta-1,4-diene-17β-carboxylic acid (4.354 g) in dichloromethane (150 ml) containing triethylamine (1.4 ml), was treated with N,N-dimethylthiocarbamoyl chloride (2.519 g) and the reaction was stirred under nitrogen at 22° C. for 80 min. Ethyl acetate (500 ml) was added and the resulting solution was successively washed with 2 N-hydrochloric acid, water, sodium hydrogen carbonate solution, water and saturated sodium chloride solution and dried and the solution was concentrated. On cooling, crystallisation occurred and the solid was filtered and dried in vacuo to give the title anhydride (3.562 g) as pale yellow prisms, m.p. 283°–287° (dec), $[\alpha]_D+156°$ (c 0.84, dimethylsulphoxide).

PREPARATION IX

6α,9α-Difluoro-11β-hydroxy-16α,17α-isopropylidenedioxy-3-oxoandrosta-1,4-diene-17β-carbothioic acid (IX)

A suspension of VIII (3.455 g) in diethylamine (200 ml) was heated under reflux under nitrogen for 6 h. The initial suspension quickly dissolved, but a pale brown suspension formed after 30 min and remained unchanged. The cooled reaction mixture was poured into water (1.0 l), acidified with concentrated hydrochloric acid (210 ml) to pH 1 and extracted with ethyl acetate. The combined extracts were washed with water, and extracted with 5% sodium carbonate solution and water and the aqueous extracts were combined. The combined extracts were acidified with 6 N-hydrochloric acid and extracted with ethyl acetate. The combined organic extracts were washed with water and saturated sodium chloride solution, then dried, and the solvent was removed in vacuo to give a pale grey solid (2.31 g). Part of the product (0.408 g) was crystallised from ethyl acetate to give the title carbothioic acid (0.149 g), m.p. 191°–199°, $[\alpha]_D+124°$ (c 1.04, dimethylsulphoxide).

PREPARATION X

6α-Fluoro-11β,17α-dihydroxy-3-oxoandrosta-1,4-diene-17β-carboxylic acid (X)

A solution of 6α-fluoroprednisolone (4.987 g) in tetrahydrofuran (50 ml) was stirred with a solution of periodic acid (10.0 g) in water (24 ml) at 22°. After 50 mins the tetrahydrofuran was evaporated and the aqueous suspension was filtered. The solid product was washed with water (300 ml) and dried to give a white solid (4.80 g). A portion (271 mg) was crystallised from methanol to give the title acid (171 mg) as white needles, m.p. 241°–248°, $[\alpha]_D+54°$ (c 0.825).

PREPARATION XI

6α-Fluoro-11β-hydroxy-3-oxo-17α-propionyloxyandrosta-1,4-diene-17β-carboxylic acid (XI)

A solution of X (4.491 g) and triethylamine (4.46 ml) in dry dichloromethane (160 ml) at −5° was stirred and treated dropwise with propionyl chloride (2.80 ml., 2.96 g) in dry dichloromethane (ca. 5 ml.) during 5 min at below 0°. After a further 20 min below 0° the reaction mixture was diluted with dichloromethane (160 ml), washed with sodium hydrogen carbonate solution, water, dried and evaporated to a white solid (5.701 g). This was stirred with diethylamine (4.60 ml, 3.24 g) in acetone (30 ml) to give a clear yellow solution. After 30 minutes the solution was concentrated, water was added (150 ml) and the resulting solution was washed with ethyl acetate (2×30 ml). The aqueous phase was acidified to pH2 using 2 N-hydrochloric acid (50 ml) with stirring and the product extracted with ethyl acetate three times. The extracts were combined, washed with water (50 ml), dried and evaporated to give a white foam (5.819 g). A portion of the foam (304 mg) was crystallised from ethyl acetate to give the title 17α-propionate (144 mg) as small plates, m.p. 244°–227°, $[\alpha]_D+3°$ (c 0.861).

PREPARATIONS XII–XXIII

Following the same general procedure as described in Preparation I but using as starting material the 17β-carboxylic acid corresponding to the desired 17β-carbothioate (process details being summarised in Table 1 below), the following compounds were prepared:

XII. 17α-Acetoxy-9α-fluoro-11β-hydroxy-16β-methyl-3-oxoandrosta-1,4-diene-17β-carbothioic acid, m.p. 178.5°–179°, $[\alpha]_D+98°$ (c 1.02).

XIII. 17α-Butyryloxy-9α-fluoro-11β-hydroxy-16β-methyl-3-oxoandrosta-1,4-diene-17β-carbothioic acid, m.p. 175°–176°, $[\alpha]_D+107°$ (c 0.96).

XIV. 9α-Fluoro-11β-hydroxy-17α-isobutyryloxy-16β-methyl-3-oxoandrosta-1,4-diene-17β-carbothioic acid, m.p. 177°–179°, $[\alpha]_D+119°$ (c 0.90).

XV. 11β-Hydroxy-3-oxo-17α-propionyloxyandrosta-1,4-diene-17β-carbothioic acid, m.p. 134°–138°, $[\alpha]_D+67°$ (c 0.66).

XVI. 11β-Hydroxy-16β-methyl-3-oxo-17α-propionyloxyandrosta-1,4-diene-17β-carbothioic acid, m.p. 159°–163°, $[\alpha]_D+113°$ (c 0.78).

XVII. 9α-Chloro-11β-hydroxy-16β-methyl-3-oxo-17α-propionyloxyandrosta-1,4-diene-17β-carbothioic acid, m.p. 167°–171°, $[\alpha]_D+128°$ (c 0.99).

XVIII. 9α-Fluoro-11β-hydroxy-16α-methyl-3-oxo-17α-propionyloxyandrosta-1,4-diene-17β-carbothioic acid, m.p. 141°–143°, $[\alpha]_D+30°$ (c 0.51).

XIX. 6α,9α-Difluoro-11β-hydroxy-16α-methyl-3-oxo-17α-propionyloxyandrosta-1,4-diene-17β-carbothioic acid, m.p. 136°–139°, $[\alpha]_D-30°$ (c 0.56).

XX. 9α-Fluoro-11β-hydroxy-16-methylene-3-oxo-17α-propionyloxyandrosta-1,4-diene-17β-carbothioic acid, m.p. 236°–239°, $[\alpha]_D-71°$ (c 0.99).

XXI. 11β-Hydroxy-3-oxo-17α-propionyloxyandrosta-4-ene-17β-carbothioic acid, m.p. 176°–177°, $[\alpha]_D+101°$ (c 0.96).

XXII. 9α-Fluoro-11β-hydroxy-16α,17α-isopropylidenedioxy-3-oxoandrosta-1,4-diene-17β-carbothioic acid, m.p. 274°–304° (dec.), $[\alpha]_D+121°$ (c 0.51, dimethylsulphoxide).

XXIII. 6α-Fluoro-11β-hydroxy-3-oxo-17α-propionyloxyandrosta-1,4-diene-17β-carbothioic acid, m.p. 189°–193°, $[\alpha]_D+72°$ (c 0.74).

TABLE I

Formation of the mixed anhydrides

| Preparation | 17β-carboxylic acid Input (g) | Cl—CSNME2 (g) | NEt3 (ml) | Solvent (CH2Cl2) (ml) | Reaction Time (days) at room temperature |
|---|---|---|---|---|---|
| XII | 5.000 | 2.940 | 1.66 | 75 | 5[1a] |
| XIII | 15.354 | 8.809 | 4.8 | 250 | 6 |
| XIV | 4.182 | 2.399 | 1.3 | 80 | 4 |
| XV | 7.148 | 4.40 | 2.6 | 150 | 6[1b] |
| XVI | 6.137 | 3.77 | 2.05 | 140 | 6[1c] |
| XVII | 5.973 | 3.350 | 1.34 | 100 | 7 |
| XVIII | 4.207 | 2.39 | 1.35 | 80 | 0.67[7,1d] |
| XIX | 2.130 | 1.80 | 0.66 | 50 | 6[4] |
| XX | 5.000 | 2.507 | 1.41 | 75 | 3 |
| XXI | 1.000 | 2.442 | 1.22 | 15 | 2.7 |
| XXII | 1.000 | 0.588 | 0.33 | 15 | 2.8[8] |
| XXIII | 6.000 | 3.55 | 2.0 | 120 | 1.25[10] |

Treatment of the mixed anhydride intermediates with diethylamine

| Preparation | NHEt2 (ml) | Reaction Time (h) at reflux | Product (g) | Crystallisation Solvent |
|---|---|---|---|---|
| XII | 50 | 5.5 | 2.104 | EA[2a] |
| XIII | 250 | 4 | 5.244 | EA[3] |
| XIV | 60 | 4.5 | 1.00 | EA |
| XV | 60 | 4 | 3.29 | EA |
| XVI | 50 | 3.5 | 1.382 | EA |

TABLE I-continued

| | | | | |
|---|---|---|---|---|
| XVII | 60 | 5.7 | 0.527 | EA |
| XVIII | 25 | 4.75 | 1.309 | A |
| XIX | 12 | 6 | 0.418 | EA |
| XX | 50 | 3.75 | 1.296 | EA[2b] |
| XXI | 15 | 4 | 0.397[6] | A[5] |
| XXII | (a) 8 (b) 16 | (a) 3 (b) 2.5 | 0.464[9] | A |
| XXIII | 60 | 4.5 | 2.88 | EA-P |

Notes:
EA = ethyl acetate.
A = acetone.
P = petrol b.p. 60–80°
[1] Portions [a]500 mg, [b]670 mg, [c]424 mg, [d]171 mg. of the intermediate dimethylthiocarbamic anhydride were removed for characterisation.
[2] Characterisation was carried out on a sample recrystallised twice more from ethyl acetate. Recoveries [a]84% [b]69%.
[3] Product was solvated with ethyl acetate (ca 0.2 mol).
[4] The intermediate dimethylthiocarbamic anhydride (1.435 g) crystallised from ethyl acetate. A portion (95 mg) was removed for characterisation.
[5] Characterisation was carried out on a sample recrystallised twice more from acetone (recovery: 73%).
[6] Product crystallised from ethyl acetate.
[7] Sodium iodide (1.46 g) was also present in the reaction.
[8] The intermediate dimethylthiocarbamic anhydride (1.123 g) crystallised from ethyl acetate. A portion (200 mg) was chromatographed (p.l.c., chloroform-acetone, 9:1) and recrystallised from ethyl acetate (recovery 65%).
[9] Reaction carried out on 781 mg of anhydride.
[10] Sodium iodide (2.13 g) was also present in the reaction.

PREPARATION XXIV

9α-Chloro-11β-hydroxy-16β-methyl-3-oxo-17α-propionyloxyandrosta-1,4-diene-17β-carbothiotic acid and 9β,11β-epoxy-16β-methyl-3-oxo-17α-propionyloxyandrosta-1,4-diene-17β-carbothioic acid (XXIV)

A solution of 17β-N,N-dimethylthiocarbamoyloxycarbonyl-9α-chloro-11β-hydroxy-16β-methyl-17α-propionyloxyandrosta-1,4-diene-3-one (5.586 g,) in diethylamine (60 ml) was refluxed under nitrogen for 5 h 40 min. The reaction was poured into water (450 ml), acidified to pH 10 with concentrated hydrochloric acid and extracted with ethyl acetate (3×60 ml). The combined extracts were washed with water then extracted with aqueous sodium carbonate solution (4×50 ml). The aqueous extracts were acidified with 6 N-hydrochloric acid to pH 1 and extracted with ethyl acetate (3×50 ml). The combined extracts were washed with water and saturated sodium chloride solution and dried and the solvent removed in vacuo to give a colourless froth (2.834 g).

Two crystallisations of the mixture from ethyl acetate gave 9α-chloro-11β-hydroxy-16β-methyl-3-oxo-17α-propionyloxyandrosta-1,4-diene-17β-carbothioic acid (0.527 g) as white prisms, m.p. 167° to 171°, $[\alpha]_D+128°$ (c 0.99). The mother liquors from the crystallisations contained an additional quantity of the above 9α-chloro-11β-hydroxycarbothioic acid together with 9β,11β-epoxy-16β-methyl-3-oxo-17α-propionyloxyandrosta-1,4-diene-17β-carbothioic acid.

PREPARATION XXV

S-Iodomethyl 9α-fluoro-11β-hydroxy-16β-methyl-3-oxo-17α-propionyloxyandrosta-1,4-diene-17β-carbothioate (XXV)

A solution of the compound of Example 1 (hereinafter disclosed) (500 mg) and sodium iodide (1.874 g) in acetone (15 ml) was stirred and heated under reflux for 6.5 h. Ethyl acetate (75 ml) was then added and the solution was washed successively with water, 10% sodium thiosulphate solution, 5% sodium hydrogen carbonate solution and water, dried and evaporated to give an off-white foam (525 mg). P.l.c. in chloroform-acetone (6:1) gave an off-white foam (478 mg) which was crystallised from acetone without being heated above room temperature to give colourless crystals of the title S-iodomethyl ester (241 mg) m.p. 196°–197°, $[\alpha]_D-32°$ (c 1.01).

PREPARATIONS XXVI—XXXVII

Following the same general procedure as described in Preparation XXV but using as starting material the S-chloromethyl 17β-carbothioate corresponding to the desired product (process details being summarised in Table II below), the following compounds were prepared XXVI. S-Iodomethyl 17α-acetoxy-9α-fluoro-11β-hydroxy-16β-methyl-3-oxoandrosta-1,4-diene-17β-carbothioate, m.p. 204°–205°, $[\alpha]_D-29°$ (c 0.98).

XXVII. S-Iodomethyl 11β-hydroxy-3-oxo-17α-propionyloxyandrosta-1,4-diene-17β-carbothioate, $[\alpha]_D+26°$ (c 0.47).

XXVIII. S-Iodomethyl 11β-hydroxy-16β-methyl-3-oxo-17α-propionyloxyandrosta-1,4-diene-17β-carbothioate, $[\alpha]_D+5°$ (c 0.74).

XXIX. S-Iodomethyl 9α-chloro-11β-hydroxy-16β-methyl-3-oxo-17α-propionyloxyandrosta-1,4-diene-17β-carbothioate, $[\alpha]_D+7°$ (c 0.36).

XXX. S-Iodomethyl 9α-fluoro-11β-hydroxy-16α-methyl-3-oxo-17α-propionyloxyandrosta-1,4-diene-17β-carbothioate, $[\alpha]_D+85°$ (c 0.55).

XXXI. S-Iodomethyl 6α,9α-difluoro-11β-hydroxy-16α-methyl-3-oxo-17α-propionyloxyandrosta-1,4-diene-17β-carbothioate.

XXXII. S-Iodomethyl 9α-fluoro-11β-hydroxy-16-methylene-3-oxo-17α-propionyloxyandrosta-1,4-diene-17β-carbothioate, m.p. 191°–199°, $[\alpha]_D-31°$ (c 0.99).

XXXIII. S-Iodomethyl 9α-fluoro-11β-hydroxy-3-oxo-17α-propionyloxyandrosta-1,4-diene-17β-carbothioate, m.p. 175°–178°, $[\alpha]_D+4°$ (c 0.50).

XXXIV. S-Iodomethyl 6α-fluoro-11β-hydroxy-3-oxo-17α-propionyloxyandrosta-1,4-diene-17β-carbothioate, m.p. 195°–197°, $[\alpha]_D+18°$ (c 0.64).

XXXV. S-Iodomethyl 17α-acetoxy-6α,9α-difluoro-11β-hydroxy-16α-methyl-3-oxoandrosta-1,4-diene-17β-carbothioate, m.p. 241°–243°, $[\alpha]_D+78°$ (c 0.78).

XXXVI. S-Iodomethyl 17α-butyryloxy-6α,9α-difluoro-11β-hydroxy-16α-methyl-3-oxoandrosta-1,4-diene-17β-carbothioate, m.p. 210°–212°, $[\alpha]_D+89°$ (c 0.90).

XXXVII. S-Iodomethyl 9α-fluoro-11β-hydroxy-16α,17α-isopropylidenedioxy-3-oxoandrosta-1,4-diene-17β-carbothioate, m.p. 261°–270° (dec.), $[\alpha]_D+97°$ (c 0.48, dimethylsulphoxide).

TABLE II

Halogen Exchanges on S-haloalkyl 17α-acyloxy-androstane-17β-carbothioates

| Preparation No. | NaI (mg) | STARTING STEROID HALIDE | STARTING STEROID INPUT (mg) | SOLVENT (acetone) (ml) | REACTION TIME (h) (at reflux) | PLC (Silica) $CHCl_3$—$Me_2CO$ | CRYSTAL-LISATION SOLVENT | PRODUCT (mg) |
|---|---|---|---|---|---|---|---|---|
| XXVI | 6632 | Cl | 1715 | 20 | 3.5 | — | EA | 216[1] |
| XXVII | 3800 | Cl | 925 | 10 | 4 | — | — | 1084 |
| XXXVIII | 3260 | Cl | 840 | 10 | 3 | — | — | 969 |
| XXIX | 1995 | Cl | 536 | 20 | 6.5 | — | — | 591 |
| XXX | 2160 | Cl | 580 | 10 | 3 | — | — | 685 |
| XXXI | 1200 | Cl | 303 | 30 | 5 | — | — | 317[3] |
| XXXII | 7361 | Cl | 1953 | 23 | 6 | 19:1 | A | 296[2] |
| XXXIII | 5500 | Cl | 1300 | 35 | 4 | — | M | 1250[7] |
| XXXIV | 8400 | Cl | 2000 | 54 | 4.5 | — | EA-P | 1800 |
| XXXV | 19000 | Cl | 4750 | 200 | 5 | — | EA | 4620[6] |
| XXXVI | 6500 | Cl | 1620 | 70 | 5.5 | — | EA | 1610[5] |
| XXXVII | 5491 | Cl | 1419 | 20 | 24 | 9:1 | A | 224[8] |

EA = ethyl acetate
A = acetone
M = methanol
P = petrol b.p. 60–80°

Notes
[1] Obtained from a portion (300 mg) of the crude product (2.024 g).
[2] Obtained from a portion (400 mg) of the crude product (2.058 g).
[3] The product was used directly for the preparation of the corresponding fluoromethyl 17β-carbothioate.
[4] Lithium chloride was used in place of sodium iodide.
[5] Solvated with 0.5 $H_2O$.
[6] Solvated with 0.1 EA.
[7] Solvated with 0.2 EA + 0.5 $H_2O$.
[8] Obtained from a portion (300 mg) of the crude crystalline product (1.611g).

PREPARATION XXXVIII

S-Iodomethyl 6α,9α-difluoro-11β-hydroxy-16α,17α-isopropylidene-dioxy-3-oxoandrosta-1,4-diene-17β-carbothioate (XXXVIII)

A solution of the compound of Example 4 hereinafter disclosed (0.795 g) in acetone (50 ml) was heated under reflux with sodium iodide (2.969 g) for 5.5 h. Ethyl acetate (75 ml) was added and the solution was washed successively with water, sodium metabisulphite solution, then dried and the solvent removed in vacuo to give an off-white solid (0.893 g). Part (0.205 g) of this was crystallised twice from ethyl acetate to give the title S-iodomethylthioester (0.105 g) as white prisms, m.p. 260°–262° (dec.), $[α]_D+81°$ (c 0.6, dimethylsulphoxide).

PREPARATION XXXIX

S-2'-Bromoethyl 9α-fluoro-11β-hydroxy-16β-methyl-3-oxo-17α-propionyloxyandrosta-1,4-diene-17β-carbothioate (XXXIX)

I (0.5 g) was treated as described for the S-chloromethyl ester (Example 1 Method A hereinafter disclosed) but using 1,2-dibromoethane to give colourless crystals of the title S-2'-bromoethyl ester (0.409 g), m.p. 174°–145°, $[α]_D+120°$ (c 1.04).

PREPARATION XL

16α,17α-Epoxy-9α-fluoro-11β-hydroxy-16β-methyl-3-oxoandrosta-1,4-diene-17β-carbothioic acid (XL)

A mixture of 16α,17α-epoxy-9α-fluoro-11β-hydroxy-16β-methyl-3-oxoandrosta-1,4-diene-17β-carboxylic acid (377 mg) and 2-fluoro-1-methylpyridinium tosylate (340 mg) in dry dichloromethane (7 ml) was stirred, cooled in ice, and treated during 1 min with triethylamine (0.42 ml). After 1 h, hydrogen sulphide was passed through the mixture for 30 min to give a yellow solution. T.l.c. (chloroform-acetone-acetic acid, 30:8:1) showed a major less polar product had formed. After being allowed to warm to room temperature during 1 h the mixture was treated with 2 N-hydrochloric acid (30 ml), and the product was extracted with ethyl acetate (3×20 ml). The acidic product was extracted from the organic phase with 5% sodium carbonate, the aqueous extracts were combined and acidified with 6 N-hydrochloric acid, then extracted with ethyl acetate. The combined acidic extracts were washed with water, dried and concentrated under reduced pressure to give, after filtration, off-white crystals (274 mg) probably largely the unstable 16α,17α-epoxy-9α-fluoro-11β-hydroxy-16β-methyl-3-oxoandrosta-1,4-diene-17β-carbothioic acid (no starting oxyacid present) as judged by t.l.c. (chloroform-acetone-acetic acid 30:8:1, $R_F$ ca 0.7).

PREPARATION XLI

S-Chloromethyl 16α,17α-epoxy-9α-fluoro-11β-hydroxy-16β-methyl-3-oxoandrosta-1,4-diene-17β-carbothioate (XLI)

Method A

A suspension of 16α,17α-epoxy-9α-fluoro-11β-hydroxy-16β-methyl-3-oxoandrosta-1,4-diene-17β-carboxylic acid (753 mg) and 2-fluoro-1-methylpyridinium tosylate (680 mg) in dichloromethane (7 ml) was treated dropwise at 0° C. with triethylamine (1.39 ml), and then stirred at 0° C. for 1 h. Hydrogen sulphide was then passed through the mixture for 15 min and then the resulting solution was stirred at 0° C. for a further 1 h. Bromochloromethane (0.26 ml) was then added and the mixture was stirred and allowed to warm to room temperature. After a further 1.5 h the reaction mixture was diluted with ethyl acetate (250 ml) and washed successively with 2 N-hydrochlorice acid, 5% sodium hydrogen carbonate solution and water, dried and evaporated to a pale yellow solid (818 mg). The solid was subjected to p.l.c. in chloroform-acetone (9:1) (two runs). The major band (515 mg) was crystallised from acetone to give white needles of the title S-chloromethyl ester epoxide (447 mg), m.p. 246°–251°, $[\alpha]_D+131°$ (c 0.67).

Method B

A suspension of 16α,17α-epoxy-9α-fluoro-11β-hydroxy-16-methylene-3-oxoandrosta-1,4-diene-17β-carboxylic acid (376 mg) and 2-chloro-N-methylbenzothiazolium trifluoromethane sulphonate (400 mg) in dichloromethane was treated dropwise at 0° C. with triethylamine (0.7 ml). The resulting solution was stirred at 0° C. for 1.25 h. and then hydrogen sulphide was passed through the mixture for 10 min. After a further 1 h at 0° C. bromochloromethane (0.13 ml) was added and the mixture was stirred at room temperature. Two more portions of bromochloromethane (0.13 ml) were then added after a further 1.5 h and 1.8 h. Fifteen min. after the final addition the reaction mixture was diluted with ethyl acetate (200 ml) and washed successively with 2 N-hydrochloric acid, 5% sodium hydrogen carbonate solution and water, dried and evaporated to a red crystalline solid. The solid was subjected to p.l.c. in chloroform-acetone (19:1) (three runs). The more polar band gave a pale pink solid, the title S-chloromethyl ester (134 mg)., identical to an authentic sample on t.l.c.

PREPARATION XLII

S-Chloromethyl 9α-fluoro-11β,17α-dihydroxy-16-methylene-3-oxoandrosta-1,4-diene-17β-carbothioate (XLII)

A solution of XLI (400 mg) in trifluoroacetic acid (16 ml) was stirred at room temperature. After 5.5 h the reaction mixture was evaporated to near dryness and the residue dissolved in ethyl acetate (100 ml). The solution was washed with 5% sodium hydrogen carbonate solution and water, dried and evaporated to a yellowish-green foam (466 mg). The foam was subjected to p.l.c. in chloroform-acetone (9:1) (three runs). A portion (80 mg) of the major band (315 mg) was crystallised twice from acetone to give white crystals of the title 16-methylene 17α-alcohol (48 mg), m.p. 242°–243°, $[\alpha]_D+36°$ (c 0.50).

PREPARATION XLIII

9α-Fluoro-17α-hydroxy-16β-methyl-3,11-dioxoandrosta-1,4-diene-17β-carboxylic acid (XLIII)

A stirred suspension of 9α-fluoro 17,21-dihydroxy-16β-methylandrosta-1,4-diene-3,11,20-trione (4.842 g) in tetrahydrofuran (50 ml) was cooled in ice and treated dropwise over 5 min with a solution of periodic acid (4.255 g) in water (15 ml). The reaction was stirred at 22° for 2.25 h, when most of the suspension had dissolved. The solvent was removed in vacuo, with periodic addition of water to maintain the original volume. The resulting precipitate was filtered off, washed with water and dried in air and in vacuo to give the title carboxylic acid as cream prisms (4.55 g) mp 270°–272° (dec), $[\alpha]_D+136°$ (c 1.04, dimethylsulphoxide).

PREPARATION XLIV

9α-Fluoro-11β,17α-dihydroxy-16β-methyl-3-oxoandrosta-1,4-diene-17β-carbothioic acid (XLIV)

A stirred solution of 9α-fluoro-11β,17α-dihydroxy-16β-methyl-3-oxoandrosta-1,4-diene-17β-carboxylic acid (0.502 g) in dry N,N-dimethylformamide (15 ml) was cooled at −5° under nitrogen and treated with N,N'-carbonyldiimidazole (0.435 g) and the reaction was stirred at −5° for 18 h. Hydrogen sulphide gas was bubbled into the reaction for 20 min and the solution was stirred for a further 4 h, gradually being allowed to warm to 22°. The reaction was poured into ethyl acetate and the resulting solution was washed with 2 N-hydrochloric acid and water, then extracted with 2 N-sodium carbonate solution (3×50 ml). The combined extracts were washed with ethyl acetate (60 ml) then covered with further ethyl acetate (100 ml) and acidified with hydrochloric acid to pH 1.0. The aqueous layer was extracted with further ethyl acetate and the extracts were washed with water and saturated sodium chloride solution, then dried and the solvent was removed in vacuo to give a white solid which was crystallised twice from ethyl acetate to give the title carbothioic acid (0.315 g) m.p. 198°–201° (dec), $[\alpha]_D+189°$ (c 0.71).

PREPARATION XLV

9α-Fluoro-17α-hydroxy-16β-methyl-3,11-dioxoandrosta-1,4-diene-17β-carbothioic acid (XLV)

A stirred solution of XLIII (5.587 g) in dry N,N-dimethylformamide (150 ml) at 20° under nitrogen was treated with N,N'-carbonyldiimidazole (4.847 g) and the reaction was stirred at 20° for 4 h. Hydrogen sulphide gas was bubbled into the reaction for 10 min and the solution was stirred for a further hour. The solution was poured onto ice (300 ml) and 2 N-hydrochloric acid (100 ml) to give a buff precipitate. This was filtered off, air-dried overnight (6.268 g) and crystallised from ethyl acetate to give the title carbothioic acid (3.761 g) as white prisms, m.p. 215°–218°, $[\alpha]_D+143°$ (c 0.88, dimethylformamide).

PREPARATION XLVI

9α-Fluoro-17α-hydroxy-16β-methyl-3,11-dioxoandrosta-1,4-diene-17β-carbothioic acid (XLVI)

A stirred solution of XLIII (1.059 g) in dry N,N-dimethylformamide (50 ml) at 20° under nitrogen was treated with N,N'-thiocarbonyldiimidazole (1.368 g) and the reaction was stirred at 20° for 4 h. Hydrogen sulphide gas was bubbled into the reaction for 5 min and the solution was stirred for a further hour. The reaction was partitioned between ethyl acetate (100 ml) and 2 N-hydrochloric acid (100 ml) and the organic phase was washed with 2 N-hydrochloric acid (100 ml) and water (2×100 ml) and was extracted with 2 N-sodium carbonate solution (2×75 ml). The combined extracts were washed with ethyl acetate (50 ml), then covered with ethyl acetate (100 ml) and acidified with hydrochloric acid to pH 1. The aqueous layer was extracted with further ethyl acetate (50 ml) and the combined extracts were washed with water, saturated sodium chloride solution, dried, and the solvent was removed in vacuo. The residue was crystallised from ethyl acetate to give the title carbothioic acid (0.559), m.p. 212°–219°, $[\alpha]_D+145°$ (c 0.81, dimethylformamide).

PREPARATION XLVII

S-Chloromethyl 9α-fluoro-11β,17α-dihydroxy-16β-methyl-3-oxoandrosta-1,4-diene-17β-carbothioate (XLVII)

A stirred solution of XLIV (0.169 g) and sodium hydrogen carbonate (0.040 g) in N,N-dimethylformamide (6 ml) was treated with bromochloromethane (0.1 ml) and stirring was continued at 22° for 1 h. The reaction mixture was diluted with ethyl acetate (100 ml) and the solution was successively washed with 2 N-hydrochloric acid, water, 2 N-sodium carbonate solution, water and saturated sodium chloride solution, then dried and the solvent was removed in vacuo. The residue was crystallised twice from ethyl acetate to give the title S-chloromethylthioester (0.193 g) as white plates solvated with ethyl acetate (1 mol), m.p. 126°–130°, $[\alpha]_D + 147.5°$ (c 0.64).

PREPARATION XLVIII

9α-Fluoro-16β-methyl-3,11-dioxo-17α-propionyloxyandrosta-1,4-diene-17β-carbothioic acid (XLVIII)

A stirred solution of XLV (0.485 g) and triethylamine (0.57 ml) in dichloromethane was cooled in ice-salt, treated with propionyl chloride (0.43 ml) and the reaction was stirred at 0° for 1.5 h. The mixture was partitioned between ethyl acetate (75 ml) and 2 N-sodium carbonate solution (75 ml) and the organic layer was successively used with further 2 N-sodium carbonate solution, water, 2 N-hydrochloric acid, water, and saturated sodium chloride solution, then dried and the solvent removed in vacuo to give a yellow crystalline solid (0.562 g). This was dissolved in acetone (10 ml), diethylamine (1.0 ml) was added and the reaction was stirred at 22° for 1.25 h. The solvents were removed in vacuo and the residue was partitioned between ethyl acetate (30 ml) and 2 N-hydrochloric acid (30 ml). The ethyl acetate layer was washed with water and extracted with 2 N-sodium carbonate solution (2×30 ml). The combined extracts were washed with ethyl acetate (30 ml) and covered with ethyl acetate (60 ml) and acidified to pH 1.0 with hydrochloric acid. The ethyl acetate layer was washed with water and saturated sodium chloride solution, then dried and the solvent was removed in vacuo to give a white solid which was crystallised twice from ethyl acetate to give the title ester (0.290 g), m.p. 173°–180°, $[\alpha]_D + 148°$ (c 1.03).

PREPARATION XLIX

S-Chloromethyl 9α-fluoro-17α-hydroxy-16β-methyl-3,11-dioxoandrosta-1,4-diene-17β-carbothioate (XLIX)

A solution of XLV (5.006 g), and sodium bicarbonate (1.612 g) in N,N-dimethylacetamide (50 ml) was treated with bromochloromethane (1.24 ml) and the reaction was stirred at 22° for 3.3 h. The solution was diluted with ethyl acetate (70 ml) and washed successively with 2 N-hydrochloric acid, water, sodium metabisulphite solution, water and saturated sodium chloride solution, then dried and the solvent was removed in vacuo to give a cream solid (3.638 g). The analytical sample was obtained after preparative t.l.c. (silica gel, developed with chloroform:acetone=9.1), and crystallised from ethyl acetate as colourless prisms of the title ester (0.262 g), m.p. 223°–228°, $[\alpha]_D + 251°$ (c 1.2).

PREPARATION L

9α-Fluoro-11β-hydroxy-16β-methyl-3-oxo-17α-propionyloxyandrosta-1,4-diene-17β-carbothioic acid (L)

A stirred solution of XLIV (0.511 g) in dichloromethane (20 ml) containing triethylamine (0.6 ml) was cooled to 2° and treated with propionyl chloride (0.45 ml) and the reaction was stirred at 2° for 2.5 h. The reaction was partitioned between ethyl acetate and sodium hydrogen carbonate and the organic phase was washed with water, 2 N-hydrochloric acid, water and saturated sodium chloride solution, dried and the solvent removed in vacuo to give a colourless solid (0.634 g). This was dissolved in acetone (30 ml), diethylamine (1.5 ml) added and the clear solution stirred at 22° for 55 min. The reaction was diluted with ethyl for 55 min. The reaction was diluted with ethyl acetate (50 ml) and was washed with 2 N-hydrochloric acid and water then extracted with 5% sodium carbonate solution. The combined extracts were acidified with 2 N-hydrochloric acid to pH 1 and extracted with ethyl acetate. The combined extracts were washed with water and saturated sodium chloride solution and dried and the solvent removed to give a colourless froth (0.522 g) which was crystallised from ethyl acetate to give the title ester as colourless prisms (0.307 g) m.p. 174°–179°, $[\alpha]_D + 107°$ (c 1.0).

PREPARATION LI

9α-Fluoro11β,17α-dihydroxy-16-methylene-3-oxoandrosta-1,4-diene-17β-carbothioic acid (LI)

A solution of 9α-fluoro-11β,17α-dihydroxy-16-methylene-3-oxoandrosta-1,4-diene-17β-carboxylic acid (0.218 g) in dry N,N-dimethylformamide (10 ml) at 22° under nitrogen was treated with N,N'-carbonylidiimidazole (0.254 g) and the reaction was stirred at 22° for 4 h. Hydrogen sulphide gas was bubbled into the reaction for 5 min and the mixture, now pale green, was stirred for 1 h at 22°. The mixture was diluted with ethyl acetate (150 ml) and the solution was washed with 2 N-hydrochloric acid, water and saturated sodium chloride solution, dried and the solvent removed in vacuo to give a yellow froth (0.222 g) which was crystallised twice from ethyl acetate to give the title carbothioic acid (0.078 g) as white prisms, decomposed at ca. 250° without melting, $[\alpha]_D + 117°$ (c 0.32).

PREPARATION LII

9α-Fluoro-11β,17α-dihydroxy-3-oxoandrosta-1,4-diene-17β-carboxylic acid (LII)

A suspension of 9α-fluoroprednisolone (10 g) in dry tetrahydrofuran (55 ml) was stirred and treated with a solution of periodic acid (9.0 g) in water (90 ml) and the mixture was stirred at 22° C. for 2 h. It was then poured into iced-water (ca 400 ml) and, after being stirred for 15 min., the solid product was collected, washed with water, and dried to give the title acid as a solid (9.42 g). A portion recrystallised from ethanol had m.p. 289°–293° $[\alpha]_D + 66°$ (c 0.73, methanol).

PREPARATION LIII

9α-Fluoro-11β,17α-dihydroxy-3-oxoandrosta-1,4-diene-17β-carbothioic acid (LIII)

A solution of 9α-fluoro-11β,17α-dihydroxy-3-oxoandrosta-1,4-diene-17β-carboxylic acid (4.5 g) in dry dimethylformamide (100 ml) was stirred under nitrogen with N,N'-carbonyldiimidazole (4.04 g) at 22° C. for 4 h. Hydrogen sulphide was then passed through the solution for 30 min and then kept for a further 15 min. The mixture was poured into a mixture of 2 N-hydrochloric acid (250 ml) and ice (ca 100 g) and the resulting precipitate was collected, washed with water and dried to give a white solid (4.56 g). A portion (120 mg) was recrystallised from ethanol to give the title thioacid as colourless crystals (70 mg), m.p. 222°–225°, $[\alpha]_D + 116°$ (c 0.57).

PREPARATION LIV

6α,9α-Difluoro-11β,17α-dihydroxy-16α-methyl-3-oxoandrosta-1,4-diene-17β-carbothioic acid (LIV)

A solution of 6α,9α-difluoro-11β,17α-dihydroxy-16α-methyl-3-oxoandrosta-1,4-diene-17β-carboxylic acid (12.0 g) is dry dimethylformamide (250 ml) was stirred and treated with N,N'-carbonyldiimidazole (9.94 g) under nitrogen at room temperature. After 4 h, hydrogen sulphide was passed through the solution for 0.5 h and the mixture was kept for a further 0.5 h. The reaction mixture was poured into 2 N-hydrochloric acid (500 ml) containing ice (ca 250 g). The resulting precipitate was collected, washed with water and dried in vacuo to give the title thioacid as a white solid (11.47 g), m.p. 230°–232°, $[α]_D+94°$ (c 0.91).

PREPARATION LV

17α-Acetoxy-6α,9α-difluoro-11β-hydroxy-16α-methyl-3-oxoandrosta-1,4-diene-17β-carbothioic acid (LV)

A solution of LIV (1.625 g) and triethylamine (2.0 ml) in dichloromethane (75 ml) was stirred at ca 0° C., treated dropwise with acetyl chloride (1.275 ml), then stirred at this temperature for 1.25 h. The mixture was washed with 2 N-sodium carbonate (50 ml), water, 2 N-hydrochloric acid (50 ml), water (3×50 ml), brine (50 ml), then dried and evaporated to a white solid (1.91 g). This was dissolved in acetone (40 ml) and stirred with diethylamine (4 ml) at 27° C. for 45 min. The mixture was concentrated to ca 25 ml and poured into 2 N-hydrochloric acid (100 ml) containing ice (ca 100 g): after being stirred the resulting precipitate was collected, washed with water and dried to give a solid (1.685 g). A portion (400 mg) was recrystallised from ethyl acetate to give the title 17α-acetate (280 mg), m.p. 175°–177°.

PREPARATION LVI

17α-Butyryloxy-6α,9α-difluoro-11β-hydroxy-16α-methyl-3-oxoandrosta-1,4-diene-17β-carbothioic acid (LVI)

Using a similar procedure to that described in Preparation LV, LIV (2.0 g) was converted, with butyryl chloride (1.5 ml) instead of acetyl chloride, to the title 17α-butyrate (2.08 g). A portion recrystallised from ethyl acetate had m.p. 155°–157°.

PREPARATION LVII

9α-Fluoro-11β-hydroxy-3-oxo-17α-propionyloxyandrosta-1,4-diene-17β-carbothioic acid (LVII)

Using a similar procedure to that described in Preparation LV, LIII (3.8 g) was converted, using propionyl chloride (3.9 ml) instead of acetyl chloride and after aminolysis of the intermediate with diethylamine (10.35 ml), into the title 17α-propionate (4.17 g). A portion (350 mg) recrystallised from ethyl acetate gave colourless crystals (165 mg), m.p. 135°–138°, $[α]_D+72°$ (c 0.92).

PREPARATION LVIII

6α,9α-Difluoro-11β-hydroxy-16α-methyl-3-oxo-17α-propionyloxyandrosta-1,4-diene-17β-carbothioic acid (LVIII)

A solution of LIV (5.0 g) and triethylamine (6.15 ml) in dichloromethane (140 ml) was cooled with ice-salt and treated dropwise with propionyl chloride (4.74 ml). The reaction mixture was stirred further at ca 0° C. for 0.75 h then washed successively with 2 N-sodium carbonate, water, 2 N-hydrochloric acid, water and brine. After being dried, solvent was removed to give a white solid (6.35 g). This was redissolved in acetone (120 ml) and diethylamine (12.5 ml): after being stirred at room temperature for 1 h the volume was reduced to ca 75 ml. The solution was poured into 2 N-hydrochloric acid (200 ml) containing ice (ca 300 g) and the resulting precipitate was collected, washed with water and dried in vacuo to a white solid (5.17 g) m.p. 152°–155°. Recrystallisation of a portion (400 ml) from ethyl acetate gave the analytically pure title thioacid 17α-propionate as colourless crystals (290 mg), m.p. 161°–164°, $[α]_D-27°$ (c 0.95), whose solid-state infrared spectrum (in Nujol) showed a different crystalline form from the sample obtained in Preparation XIX.

PREPARATION LIX

S-Chloromethyl 9α-fluoro-16β-methyl-3,11-dioxo-17α-propionyloxyandrosta-1,4-diene-17β-carbothioate (LIX)

A solution of XLIX (409 mg) in propionic acid (5 ml), trifluoroacetic anhydride (2 ml) and toluene p-sulphonic acid (0.1 ml of dry chloroform solution, 80 mg/ml) was stirred at 22° C. for 2.75 days. The non-acidic product was isolated by extraction with ethyl acetate after being poured into saturated sodium hydrogen carbonate. The crude material was chromatographed on silica in chloroform-acetone (14:1) and crystallised from ethyl acetate-petrol (b.p. 60°–80° C.) to give the title 17α-propionate as colourless crystals, m.p. 205°–206°, $[α]_D+95°0$ (c 1.15).

PREPARATION LX

S-Chloromethyl 9α-fluoro-11β,17α-dihydroxy-16β-methyl-3-oxoandrosta-1,4-diene-17β-carbothioate (LX)

A suspension of XLIX (102 mg) in ethanol (2.5 ml) was stirred with sodium borohydride (10 mg) at 22° C. for 1 h. The reaction mixture was treated with acetone (5 ml) then concentrated to near dryness: the residue the dissolved in ethyl acetate (25 ml), washed with N-hydrochloric acid, water, and brine. After being dried the organic solvent was removed to give the title 11β-alcohol as a colourless foam (103 mg) whose sole major component was equipolar with an authentic specimen on t.l.c. comparison (silica, chloroformacetone, 9:1).

PREPARATION LXI

9α-Fluoro-11β-hydroxy-16β-methyl-3-oxo-17α-propionyloxyandrosta-1,4-diene-17β-carbothioic acid (LXI)

Method A

A solution of 9α-fluoro-11β-hydroxy-16β-methyl-3-oxo-17α-propionyloxyandrosta-1,4-diene-17β-carboxylic acid (603 mg, 0.75 mol ethyl acetate solvate) and N,N'-carbonyldi(1,2,4-triazole) (0.997 mg) in dry dimethylformamide (45 ml) was stirred under nitrogen at ca 22° C. for 18.5 h. A solution (15 ml) prepared from sodium hydride (305 mg) in dimethylformamide by saturating with hydrogen sulphide, was added and stirring was continued at ambient temperature for 3 days. The reaction mixture was poured into 2 N-hydrochloric acid (200 ml) and the product was extracted with ethyl acetate (3×). The organic extracts were combined, washed with water and back extracted with 5% sodium carbonate solution: the alkaline extracts were acidified with hydrochloric acid and extracted with ethyl acetate (3×). After being washed with water and brine the organic extracts were dried and concentrated to low volume: the title thioacid separated as cream crystals (101 mg), whose sole major component was identified by comparison with an authentic specimen by $^1$H nmr and by t.l.c. (silica, chloroform-acetone 4:1).

Method B

A solution of 9α-fluoro-11β-hydroxy-16β-methyl-3-oxo-17α-propionyloxyandrosta-1,4-diene-17β-carboxylic acid (701 mg, 0.75 mol ethyl acetate solvate) and N,N'-carbonyldiimidazole (473 mg) in dry dimethylformamide (26 mg) was stirred under nitrogen at ca 22° C. for 19.5 h., then treated with a solution (10 ml) of sodium hydride (60% dispersion in oil, 233 mg) in dimethylformamide (10 ml) saturated with hydrogen sulphide. The resulting mixture was then stirred at ambient temperature for 5.5 h. The reaction mixture was diluted with ethyl acetate (100 ml) and washed with 2 N-hydrochloric acid, water and brine, then dried and evaporated to a froth (186 mg). The title thioacid was shown to be the major component in the produced by $^1$H nmr and by t.l.c. (silica, chloroform-acetone [4:1], and chloroform-acetone-acetic acid [30:8:1]) comparison with an authentic specimen.

Method C

In an almost identical reaction to that described in Method A the carboxylic acid was treated with 1,1'-carbonyldibenzotriazole (1.587 g) instead of N,N'-carbonyldi(1,2,4-triazole), at room temperature for 6 h. After the addition of the solution obtained from hydrogen sulphide and sodium hydride in dimethylformamide, reaction was continued for 41.5 h. The crude product was obtained as a foam; t.l.c. (silica, chloroform-acetone, 4:1, and chloroform-acetone-acetic acid 30:8:1) showed the title thioacid was present as a major component by comparison with an authentic specimen.

PREPARATION LXII

S-Chloromethyl 6α,9α-difluoro-16α-methyl-3-oxo-17α-propionyloxy-11β-trifluoroacetoxyandrosta-1,4-diene-17β-carbothioate (LXII)

A solution of the compound of Example 5 (hereinafter disclosed) (100 mg) in dry tetrahydrofuran (2 ml) and pyridine (0.1 ml) was treated with trifluoroacetic anhydride (0.05 ml) and the mixture was kept at room temperature for 0.5 h. The reaction mixture was poured into water and the product was extracted with ethyl acetate (3×). The organic extracts were washed with water, dried and evaporated to give the homogenous title trifluoroacetate (116 mg) according to $^1$H nmr spectroscopy (singlet at 8.59τ, 19-protons, in deuteriochloroform) and t.l.c. on silica (acetone-petrol, b.p. 40°-60° C., 1:3). An analytical sample from ether-pentane had m.p. 158°-162°, $[\alpha]_D +56°$ (c 0.23).

EXAMPLE 1

S-Chloromethyl 9α-fluoro-11β-hydroxy-16β-methyl-3-oxo-17α-propionyloxyandrosta-1,4-diene-17β-carbothioate Method A A solution of I (2.115 g) in dimethylacetamide (7 ml) was treated with sodium hydrogen carbonate (592 mg) and bromochloromethane (0.46 ml) and the mixture was stirred at room temperature. After 2 h, the reaction mixture was diluted with ethyl acetate (500 ml) and washed with 5% sodium hydrogen carbonate solution and water, dried and evaporated to give an orange foam (1.560 g). P.l.c. in chloroform-acetone (19:1) gave an off-white foam (803 mg) which was crystallised twice from methanol to give off-white needles of the title S-chloromethyl ester (668 mg), m.p. 212°-214° C., $[\alpha]_D +44°$ (c 1.06).

Method B

The title compound was similarly prepared using chloroiodomethane instead of bromochloromethane.

Method C

Sodium borohydride (19 mg) was added to a solution of II (230 mg) in ethanol (3.5 ml) and the solution was stirred at room temperature. After 20 min acetone (1 ml) was added and the solution was concentrated to ca. ¼ volume. Ethyl acetate (30 ml) was then added and the solution was washed with N-hydrochloric acid and water, dried and evaporated to give a white foam (239 mg). P.l.c. in chlorofrom-acetone (19:1) gave a white foam (188 mg) which was crystallised twice from methanol to give white needles of the title S-chloromethyl ester (158 mg) m.p. 210°-212°, $[\alpha]_D +44°$ (c 1.07).

EXAMPLE 2

S-Chloromethyl 9α-fluoro-11β-hydroxy-16α-methyl-3-oxo-17α-propionyloxyandrosta-1,4-diene-17β-carbothioate A solution of IV (0.927 g) in dimethylacetamide (4 ml) was treated with sodium hydrogen carbonate (0.256 g) and bromochloromethane (0.20 ml) and the mixture was stirred at 22° C. for 2 h. The reaction mixture was partitioned between ethyl acetate (100 ml) and 2 N-hydrochloric acid (20 ml) and the aqueous layer extracted further with ethyl acetate. The combined extracts were washed successively with 2 N-hydrochloric acid, water, 3% sodium hydrogen carbonate, water and saturated brine. After being dried the solvent was removed and the crude product (757 mg) was crystallised twice from acetone to give the title chloromethyl thiolester (0.367 g), m.p. 247°-250°, $[\alpha]_D +50.5°$ (c 0.63).

EXAMPLE 3

S-Chloromethyl 11β-hydroxy-3-oxo-17α-propionyloxyandrosta-1,4-diene-17β-carbothioate A solution of crude XV (2.366 g) in dimethylacetamide (10 ml) was treated with sodium hydrogen carbonate (756 mg) and bromochloromethane (0.59 ml) at 22° C. for 16 h. It was partitioned between ethyl acetate and 2 N-hydrochloric acid and the aqueous layer was extracted further with ethyl acetate. The combined organic phases were washed successively with 2 N-hydrochloric acid, water, sodium hydrogen carbonate, water, saturated brine then dried and the solvent was removed to give a yellow froth. The neutral product was purified by preparative h.p.l.c. on silica (15μ) in 7% acetone in chloroform and the major product crystallised from acetone to give the title chloromethyl thiolester (0.511 g), m.p. 117°–120°, $[\alpha]_D+56°$ (c 1.3).

EXAMPLE 4

S-Chloromethyl 6α,9α-Difluoro-11β-hydroxy-16α,17α-isopropylidenedioxy-3-oxoandrosta-1,4-diene-17β-carbothioate A stirred solution of IX (1.360 g) in N,N-dimethylacetamide (10 ml) was treated with sodium hydrogen carbonate (0.377 g) and bromochloromethane (0.3 ml) and stirring was continued for 1.5 h. Ethyl acetate (100 ml) was added and the resulting solution was successively washed with 2N-hydrochloric acid, water, sodium metabisulphite solution, water, sodium bicarbonate solution, water and saturated sodium chloride solution, then dried and the solution was concentrated, whereupon crystallisation occurred. The crystallised product (0.765 g) was purified by p.l.c. on silica gel, developed with chloroform:acetone (9:1). The main band was eluted with ethyl acetate and wasy crystallised from ethyl acetate to give the title S-chloromethyl thioester (0.475 g) as white prisms, m.p. 271°–278°, $[\alpha]_D+116°$, (c 0.96, dimethylsulphoxide).

EXAMPLE 5

S-Chloromethyl 6α,9α-difluoro-11β-hydroxy-16α-methyl-3-oxo-17α-propionyloxyandrosta-1,4-diene-17β-carbothioate A solution of XIX (0.546 g) in dimethylacetamide (3 ml) was treated with sodium hydrogen carbonate (202 mg) and bromochloromethane (0.16 ml) at 22° for 3 h. The mixture was treated with 2 N hydrochloric acid (50 ml) and the product was extracted with ethyl acetate. The extracts were combined and washed successively with 2 N hydrochloric acid, water, saturated brine, dried and the solvent was removed. Two crystallisations from ethyl acetate gave the title chloromethyl thiolester (0.404 g), m.p. 272°–275°, $[\alpha]_D+49°$ (c 0.35).

EXAMPLE 6–15

Following the same general procedure as Example 1 (Method A) but using as starting material the 17β-carbothioic acid corresponding to the desired 17β-carbothioate (process details being summarised in Table III below), the following compounds were prepared:

6. S-Chloromethyl 11β-hydroxy-16β-methyl-3-oxo-17α-propionyloxyandrosta-1,4-diene-17β-carbothioate, m.p. 192°–193°, $[\alpha]+65°$ (c 1.05).
7. S-Chloromethyl 9α-fluoro-11β-hydroxy-16-methylene-3-oxo-17α-propionyloxyandrosta-1,4-diene-17β-carbothioate, m.p. 212°–221°, $[\alpha]_D-56°$ (c 0.99).
8. S-Chloromethyl 17α-acetoxy-9α-fluoro-11β-hydroxy-16β-methyl-3-oxoandrosta-1,4-diene-17β-carbothioate, m.p. 220°–223°, $[\alpha]_D+39.5°$ (c 1.06).
9. S-Chloromethyl 17α-butyryloxy-9α-fluoro-11β-hydroxy-16β-methyl-3-oxoandrosta-1,4-diene-17β-carbothioate, m.p. 172°–175°, $[\alpha]_D+46°$ (c 1.10).
10. S-Chloromethyl 9α-fluoro-11β-hydroxy-17α-isobutyryloxy-16β-methyl-3-oxoandrosta-1,4-diene-17β-carbothioate, m.p. 234°–239°, $[\alpha]_D+43°$ (c 1.00).
11. S-Chloromethyl 9α-fluoro-11β-hydroxy-3-oxo-17α-propionyloxyandrosta-1,4-diene-17β-carbothioate, m.p. 196°–199°, $[\alpha]_D+38°$ (c 0.97).
12. S-Chloromethyl 6α-fluoro-11β-hydroxy-3-oxo-17α-propionyloxyandrosta-1,4-diene-17β-carbothioate, m.p. 188°–191°, $[\alpha]_D+48°$ (c 0.91).
13. S-Chloromethyl 17α-acetoxy-6α,9α-difluoro-11β-hydroxy-16α-methyl-3-oxoandrosta-1,4-diene-17β-carbothioate, m.p. 280°–283°, $[\alpha]_D+45°$ (c 0.80).
14. S-Chloromethyl 17α-butryloxy-6α,9α-difluoro-11β-hydroxy-16α-methyl-3-oxoandrosta-1,4-diene-17β-carbothioate, m.p. 235°–238°, $[\alpha]_D+49°$ (c 0.65).
15. S-Chloromethyl 9α-fluoro-11β-hydroxy-16α,17α-isopropylidenedioxy-3-oxoandrosta-1,4-diene-17β-carbothioate, m.p. 276°–280° (dec), $[\alpha]_D+127°$ (c 0.51, dimethylsulphoxide).

TABLE III

| Ex. No. | REAGENT (ml) | NaHCO$_3$ (mg) | STEROID INPUT (mg) | SOLVENT (DMA) (ml) | REACTION TIME (h) at room temperature | PLC (Silica) CHCl$_3$—Me$_2$CO | CRYSTALLISATION SOLVENT | PRODUCT (mg) |
|---|---|---|---|---|---|---|---|---|
| 6 | BrCH$_2$Cl (0.25) | 300 | 981 | 5 | 3 | — | EA | 826 |
| 7 | BrCH$_2$Cl (0.58) | 749 | 2000 | 11 | 1.5 | 19:1 | EA | 201 |
| 8 | BrCH$_2$Cl (0.44) | 565 | 1955 | 7 | 2.0 | — | EA | 307* |
| 9 | BrCH$_2$Cl (0.32) | 421 | 1501 | 10 | 1.8 | 14:1 | EA | 871 |
| 10 | BrCH$_2$Cl (0.084) | 121 | 385 | 3 | 2.75 | — | EA | 255 |
| 11 | BrCH$_2$Cl (0.90) | 1100 | 2750 | 20 | 1.25 | — | M | 1600 |
| 12 | BrCH$_2$Cl (0.86) | 1080 | 2740 | 20 | 2 | — | EA-P | 2460 |
| 13 | BrCH$_2$Cl (2.00) | 2500 | 6600 | 40 | 1.75 | — | A | 5410 |
| 14 | BrCH$_2$Cl (1.40) | 1600 | 4600 | 46 | 2 | — | A | 2140 |
| 15 | BrCH$_2$Cl | 615 | 1600 | 12 | 1.5 | 4:1 | A | 244** |

TABLE III-continued

| Ex. No. | REAGENT (ml) | NaHCO₃ (mg) | STEROID INPUT (mg) | SOLVENT (DMA) (ml) | REACTION TIME (h) at room temperature | PLC (Silica) CHCl₃—Me₂CO | CRYSTAL-LISATION SOLVENT | PRODUCT (mg) |
|---|---|---|---|---|---|---|---|---|
| | (0.48) | | | | | | | |

Notes:
EA = ethyl acetate
A = acetone
M = methanol
P = petrol b.p. 60–80°
*Obtained from a portion (400 mg) of the crude product (2.35 g).
**Obtained from a portion (300 mg) of the crude product (1.72 g).

EXAMPLE 16

S-Chloromethyl 9α-chloro-11β-hydroxy-16β-methyl-3-oxo-17α-propionyloxyandrosta-1,4-diene-17β-carbothioate and S-Chloromethyl 9β,11β-epoxy-16β-methyl-3-oxo-17α-propionyloxyandrosta-1,4-diene-17β-carbothioate A solution of the mixture XXIV (1.032 g) in dimethylacetamide (5 ml) was treated with sodium bicarbonate (0.203 g) followed by bromochloromethane (0.2 ml) and the reaction was stirred at 22° C. for 1.5 h, when it was partitioned between ethyl acetate (50 ml) and 2 N-hydrochloric acid (35 ml). The aqueous phase was extracted with futher ethyl acetate (2×30 ml) and the combined extracts were washed with 2 N-hydrochloric acid, water, saturated sodium bicarbonate solution, water, saturated sodium chloride solution and dried and the solvent removed in vacuo to give a cream froth (0.856 g) containing a mixture of the title S-chloromethyl esters.

These were separated by p.l.c. on silica, developed with chloroform:acetone (19:1). The more polar component (0.306 g) was crystallised twice from ethyl acetate to give S-chloromethyl 9α-chloro-11β-hydroxy-16β-methyl-3-oxo-17α-propionyloxyandrosta-1,4-diene-17β-carbothioate (0.232 g) as white plates, m.p. 222°–229°, $[\alpha]_D+70°$ (c 1.23).

The less polar component (0.210 g) was crystallised from acetone-petrol to give S-chloromethyl 9β,11β-epoxy-16β-methyl-3-oxo-17α-propionyloxyandrosta-1,4-diene-17β-carbothioate (0.065 g), m.p. 169°–173°, $[\alpha]_D+49°$ (c 0.60).

EXAMPLE 17

S-Fluoromethyl 9α-fluoro-11β-hydroxy-16β-methyl-3-oxo-17α-propionyloxyandrosta-1,4-diene-17β-carbothioate XXV (660 mg) was stirred with a suspension of silver fluoride (1.421 g) in acetonitrile (8.5 ml) in the dark at room temperature. After 72 h the reaction mixture was diluted with ethyl acetate (200 ml) and filtered through a pad of kieselguhr. The filtrate was washed with water, dried and evaporated to give a white foam (517 mg). P.l.c. in chloroform-cyclohexane (19:1) and chloroform gave an off-white foam (270 mg) which was crystallised from methanol, then methanol-diethyl ether to give the title S-fluoromethyl ester (176 mg), m.p. 241°–242° C., $[\alpha]_D+97.5°$ (c 0.98).

EXAMPLE 18

S-Fluoromethyl 9α-fluoro-11β-hydroxy-16α-methyl-3-oxo-17α-propionyloxyandrosta-1,4-diene-17β-carbothioate A solution of XXX (0.640 g) in acetonitrile (8 ml) was treated with dry silver fluoride (1.511 g) and stirred in the dark at 22° C. for 46.5 h. The mixture was diluted with ethyl acetate (200 ml) and filtered through kieselguhr. The solution was washed with 2 N-hydrochloric acid, water and saturated sodium chloride solution and the solvent removed in vacuo to give a pale yellow froth (0.504 g). This was chromatographed (p.l.c.) on silica gel, developed with 5% acetone in chloroform. The major band was eluted with ethyl acetate and crystallised twice from acetone to give the title fluoromethyl thioester (0.244 g), m.p. 242°–243° (dec), $[\alpha]_D+37°$ (c 0.75).

EXAMPLE 19

S-Fluoromethyl 6α,9α-Difluoro-11β-hydroxy-16α-methyl-17α-propionyloxy-3-oxoandrosta-1,4-diene-17β-carbothioate A solution of XXXI (310 mg) in acetonitrile (10 ml) was stirred with silver fluoride (947 mg) for 3 days at room temperature in the dark. Ethyl acetate (100 ml) was added and the mixture was filtered through kieselguhr. The filtrate was washed successively with 2 N-hydrochloric acid, water, saturated brine, then dried. The solvent was removed and the residue was subjected to p.l.c. in chloroform then chloroform-acetone (19:1). The product was eluted with ethyl acetate and crystallised on concentration of the solution to give the title fluoromethyl thioester (0.075 g) m.p. 272°–273° (dec), $[\alpha]_D+30°$ (c 0.35).

EXAMPLE 20

S-Fluoromethyl 9α-fluoro-11β-hydroxy-16α,17α-isopropylidenedioxy-3-oxoandrosta-1,4-diene-17β-carbothioate A suspension of XXXVII (1.290 g) in acetonitrile (20 ml) was stirred with silver(I) fluoride (2.842 g) at room temperature in the dark. After 11 days (no starting iodide remained, t.l.c. (chloroform, six runs)) the reaction mixture was diluted with ethyl acetate (400 ml) and filtered through kieselguhr. The filtrate was evaporated to a pale yellow crystalline solid (726 mg) and the kieselguhr was extracted continuously with ethyl acetate in a Soxhlet apparatus to give a yellow solid (197 mg). The solid from the filtrate was suspended in chloroform-methanol (10:1) and the insoluble fraction (203 mg) was collected. This was combined with the solid from the Soxhlet extraction in ethyl acetate (300 ml)

and filtered through a column of silica (Merck Kieselgel 60) (50 g). The eluates containing the product (t.l.c.) were combined, washed with water, dried with simultaneous treatment with charcoal and concentrated to a low volume. The resulting white solid (276 mg) was collected and recrystallised from ethyl acetate to give colourless crystals of the title S-fluoromethyl ester (231 mg), m.p. 320°–322° C. (dec.), $[\alpha]_D+132°$ (c 0.22, dimethylsulphoxide).

EXAMPLE 21

S-Fluoromethyl 6α,9α-Difluoro-11β-hydroxy-16α,17α-isopropylidenedioxy-3-oxoandrosta-1,4-diene-17β-carbothioate A solution of XXXVIII (0.804 g) in acetonitrile (60 ml) was treated with silver fluoride (1.821 g) and the reaction was stirred in the dark for 18 h. The reaction was diluted with ethyl acetate and filtered through kieselguhr. The filtrate was washed with water and saturated sodium chloride solution then dried and the solvent removed in vacuo to give a pale cream solid (0.636 g). This was purified by p.l.c. on silica gel developed twice with chloroform:acetone (14:1). The major band was eluted with ethyl acetate and crystallised five times from ethyl acetate to give the title S-fluoromethyl thioester (0.118 g) as white prisms, m.p. 305°–311° C., $[\alpha]_D+125°$ (c 0.73, dimethylsulphoxide).

EXAMPLES 22–30

Following the same general procedure as Example 17 but using as starting material the S-iodomethyl 17β-carbothioate corresponding to the desired product (process details being summarised in Table IV below), the following compounds were prepared:

22. S-Fluoromethyl 17α-acetoxy-9α-fluoro-11β-hydroxy-16β-methyl-3-oxoandrosta-1,4-diene-17β-carbothioate, m.p. 248°–249°, $[\alpha]_D+101°$ (c 1.08).
23. S-Fluoromethyl 11β-hydroxy-3-oxo-17α-propionyloxyandrosta-1,4-diene-17β-carbothioate, m.p. 112°–117°, $[\alpha]_D+67°$ (c 0.76).
24. S-Fluoromethyl 11β-hydroxy-16β-methyl-3-oxo-17α-propionyloxyandrosta-1,4-diene-17β-carbothioate, m.p. 223°–225°, $[\alpha]_D+103°$ (c 0.38).
25. S-Fluoromethyl 9α-chloro-11β-hydroxy-16β-methyl-3-oxo-17α-propionyloxyandrosta-1,4-diene-17β-carbothioate, m.p. 182°–193°, $[\alpha]_D+116°$ (c 0.75).
26. S-Fluoromethyl 9α-fluoro-11β-hydroxy-16-methylene-3-oxo-17α-propionyloxyandrosta-1,4-diene-17β-carbothioate, m.p. 205°–215°, $[\alpha]_D-58°$ (c 1.00).
27. S-Fluoromethyl 9α-fluoro-11β-hydroxy-3-oxo-17α-propionyloxyandrosta-1,4-diene-17β-carbothioate, m.p. 207°–211°, $[\alpha]_D+70°$ (c 0.88).
28. S-Fluoromethyl 6α-fluoro-11β-hydroxy-3-oxo-17α-propionyloxyandrosta-1,4-diene-17β-carbothioate, m.p. 224°–255°, $[\alpha]_D+70°$ (c 0.79).
29. S-Fluoromethyl 17α-acetoxy-6α,9α-difluoro-11β-hydroxy-16α-methyl-3-oxoandrosta-1,4-diene-17β-carbothioate, m.p. 308°–310° $[\alpha]_D+29°$ (c 0.80).
30. S-Fluoromethyl 17α-butyryloxy-6α,9α-difluoro-11β-hydroxy-16α-methyl-3-oxoandrosta-1,4-diene17β-carbothioate, m.p. 249°–252°, $[\alpha]_D+32°$ (c 1.05).

| | | | | | S-Fluoromethyl 17α-acyloxyandrostane-17β-carbothioates via halogen exchange | | | |
|---|---|---|---|---|---|---|---|---|
| Ex. No. | Ag F (mg) | STARTING STEROID HALIDE | INPUT mg | SOLVENT (MeCN) (ml) | REACTION TIME (h) at room temperature | PLC (Silica) CHCl$_3$—Me$_2$CO | CRYSTALLISATION SOLVENT | PRODUCT (mg) |
| 22 | 3745 | I | 1702 | 22 | 20 | 24:1 | A | 477 |
| 23 | 2071 | I | 1034 | 10 | 26 | 19:1 | EA | 585* |
| 24 | 1945 | I | 850 | 6 | 26 | 19:1 | EA | 166 |
| 25 | 1161 | I | 550 | 8 | 23.5 | 19:1 | M | 106 |
| 26 | 3574 | I | 1658 | 26 | 24 | 19:1 | A | 300 |
| 27 | 700 | I | 1000 | 50 | 3 | — | M | 470 |
| 28 | 462 | I | 700 | 35 | 2 | — | EA-P | 350 |
| 29 | 2600 | I | 4000 | 200 | 0.75 | — | EA | 2280 |
| 30 | 780 | I | 1200 | 60 | 1 | — | EA | 755 |

EA = ethyl acetate
A = acetone
M = methanol
P = petrol b.p. 60–80°
*Purity ca. 95%

EXAMPLE 31

S-Bromomethyl 9α-fluoro-11β-hydroxy-16β-methyl-3-oxo-17α-propionyloxyandrosta-1,4-diene-17β-carbothioate A solution of XXV (660 mg) in acetone (20 ml) was stirred with lithium bromide (972 mg) at room temperature for 5 days. The reaction mixture was diluted with ethyl acetate (150 ml) and then washed successively with 10% sodium thiosulphate solution, water and brine, dried and evaporate to an off-white foam (624 mg). This was crystallised twice from acetone-petroleum ether (m.p. 40°–60°) to give colourless crystals of the title S-bromomethyl ester (499 mg) m.p. 186.5°–187° C., $[\alpha]_D+2°$ (c 0.99).

EXAMPLE 32

S-Bromomethyl 6α,9α-difluoro-11β-hydroxy-16α-methyl-3-oxo-17α-propionyloxyandrosta-1,4-diene-17β-carbothioate A solution of XXXI (850 mg) in acetone (25 ml) was stirred with lithium bromide (1.21 g) at ca 22° C. for 5 days. The product was isolated as described for Example 31 and recrystallised twice from ethyl acetate to give colourless crystals (690 mg). These were retreated under the same reaction conditions for a further 4 days to give the pure title S-bromomethyl ester (600 mg), colourless crystals from ethyl acetate, m.p. 255°–257°, $[\alpha]_D+62°$ (c 0.82).

EXAMPLE 33

S-2'-Fluoroethyl 9α-fluoro-11β-hydroxy-16β-methyl-3-oxo-17α-propionyloxyandrosta-1,4-diene-17β-carbothioate A solution of XXXIX (910 mg) in acetonitrile (20 ml) was stirred with silver(I) fluoride (2.071 g) at room temperature in the dark. After 6 days the reaction mixture was diluted with ethyl acetate (150 ml) and filtered through kieselguhr. The filtrate was diluted with more ethyl acetate (150 ml) and washed with water, dried and evaporated to a white foam (704 mg) P.l.c. in chloroform-acetone (9:1) gave the less polar product, as a yellow foam (431 mg), which was crystallised twice from methanol to give the title S-2'-fluoroethyl ester (253 mg), m.p. 133°–134° C., $[\alpha]_D + 104.5°$ (c 0.98).

EXAMPLE 34

S-Chloromethyl 9α-fluoro-11β-hydroxy-16-methylene-3-oxo-17α-propionyloxyandrosta-1,4-diene-17β-carbothioate A suspension of XLII (227 mg) in propionic acid (2.2 ml) and trifluoroacetic anhydride (0.7 ml) was treated with a dry chloroform solution of toluene-p-sulphonic acid (0.044 ml, c ca 80 mg/ml) and then stirred at room temperature for 6 h, and then stirred at 3° C. for 16.5 h. The reaction mixture was diluted with 5% sodium hydrogen carbonate solution (75 ml) and extracted with ethyl acetate. The combined extracts were washed with water and brine, dried and evaporated to a brown gum (254 mg). The gum was subjected to p.l.c. in chloroform-acetone (19:1) (three runs). The major band (152 mg) was crystallised twice from ethanol to give white crystals (30 mg) of the title S-chloromethyl ester 17α-propionate contaminated with S-chloromethyl 9α-fluoro-17α-hydroxy-16-methylene-3-oxo-11β-propionyloxyandrosta-1,4-diene-17β-carbothioate as shown by $^1$Hnmr spectroscopy.

EXAMPLE 35

S-Chloromethyl 11β-hydroxy-16β-methyl-3-oxo-17α-propionyloxyandrost-4-ene-17β-carbothioate Catalytic reduction of the compound of Example 6 (0.517 g) in the presence of tris(triphenylphosphine)-chlororhodium(I) (497 mg) in benzene (50 ml) for 22 h afforded, after chromatography (p.l.c.) on silica in chloroform (four runs), elution with ethyl acetate, and crystallisation twice from ethyl acetate, the title $\Delta^4$-3-ketone (0.130 g), m.p. 176°–177°, $[\alpha]_D + 78°$ (c 0.80).

EXAMPLE 36

S-Chloromethyl 9α-fluoro-11β-hydroxy-16β-methyl-3-oxo-17α-propionyloxyandrost-4-ene-17β-carbothioate Catalytic reduction of the compound of Example 1 (0.646 g) with tris(triphenylphosphine)chlororhodium(I) (800 mg) in benzene (100 ml) for 21.5 h afforded, after chromatography on silica in chloroform-acetone (9:1) and two crystallisations from acetone, the title chloromethyl thiolester (0.142 g) as white needles, m.p. 217°–225°, $[\alpha]_D + 54°$ (c 0.83).

EXAMPLE 37

S-Fluoromethyl 11β-hydroxy-16β-methyl-3-oxo-17α-propionyloxyandrost-4-ene-17β-carbothiate Catalytic reduction of the compound of Example 24 (0.413 g) in the presence of tris(triphenylphosphine)-chlororhodium(I) (432 mg) in benzene (60 ml) at 22° C. for 24 h afforded, after multiple chromatography on silica in chloroform-acetone mixtures and crystallisation from acetone, the title $\Delta^4$-3-ketone (0.106 g) m.p. 174°–177° C., $[\alpha]_D + 123°$ (c 0.55).

EXAMPLE 38

S-Chloromethyl 9α-fluoro-11β-hydroxy-16β-methyl-3-oxo-17α-propionyloxyandrosta-1,4-diene-17β-carbothioate S-Chloromethyl 9β,11β-epoxy-16β-methyl-3-oxo-17α-propionyloxyandrosta-1,4-diene-17β-carbothioate (ca 0.9 mg) from Example 16 was treated with hydrogen fluoride-urea complex (ca 1 ml) and stirred for a total of 24 h at room temperature. The mixture was treated with sodium hydrogen carbonate and the product was extracted twice with ethyl acetate: the extracts were washed twice with water, dried, and evaporated. The resulting product was shown by t.l.c. on silica in three different solvent systems (acetone-petrol, b.p. 40°–60° C., 1:2; chloroform-acetone, 9:1, ethyl acetate-petrol, b.p. 40°–60° C., 1:2, two runs) to contain the title fluorohydrin by comparison with an authentic specimen.

EXAMPLE 39

S-Chloromethyl 6α,9α-fluoro-11β-hydroxy-16α-methyl-3-oxo-17α-propionyloxyandrosta-1,4-diene-17β-carbothioate A solution of LXII (29 mg) in methanol (2 ml) was kept at room temperature for 3 h. The mixture was evaporated to dryness to give the title 11β-alcohol (25 mg) identified by comparison of its $^1$H nmr spectrum (in deuteriodimethylsulphoxide) and t.l.c. properties (silica, acetone-petrol b.p. 40°–60° C., 1:3) with those of an authentic specimen.

There are also provided pharmaceutical compositions for use in anti-inflammatory therapy, comprising at least one androstane compound of formula (I) (as defined above), together with one or more pharmaceutical carriers or excipients. Such compositions may be in forms adapted for topical or internal administration.

The active androstane compounds may advantageously be formulated in conventional manner into preparations suitable for topical administration with the aid of a topical vehicle therefor. By topical administration as used herein, we include administration by insufflation and inhalation. Examples of various types of preparation for topical administration include ointments, lotions, creams, powders, drops, (e.g. eye or ear drops), sprays, (e.g. for the nose, throat, lung or skin), suppositories, retention enemas, chewable or suckable tablets or pellets (e.g. for the treatment of aphthous ulcers), capsules or cartridges for use in an inhaler or insufflator, and aerosols, (e.g. for the nose, throat or lung).

Ointments and creams, may, for example, be formulated with an aqueous or oily base with the addition of suitable thickening and/or gelling agents and/or solvents. Such base may thus, for example, include water and/or an oil such as liquid paraffin or a vegetable oil such as arachis oil or castor oil, or a solvent such as a polyethylene glycol having an average molecular weight in the range 200-600. Thickening agents which may be used according to the nature of the base include soft paraffin, aluminium stearate, cetostearyl alcohol, polyethylene glycols having an average molecular weight in the range 4,000-6,000, woolfat and beeswax and/or glyceryl monostearate and/or non-ionic emulsifying agents.

Spray compositions may for example be formulated as aqueous solutions or suspensions or as aerosols with the use of a suitable propellant, e.g. dichlorodifluoromethane, trichlorofluoromethane, dichlorotetrafluoroethane, carbon dioxide or other suitable gas.

Capsules and cartridges for use in an inhaler or insufflator, of e.g. gelatin, may be formulated containing a powder mix of a compound of the invention and a suitable powder base such as lactose or starch. Each capsule or cartridge may generally contain between 20 µg-10 mg of the active androstane compound.

The proportion of the active androstane compound in the topical compositions according to the invention depends on the precise type of formulation to be prepared but will generally be within the range of from 0.001 to 5.0% weight. Generally, however for most types of preparations advantageously the proportion used will be within the range of from 0.005 to 0.5% and preferably 0.01 to 0.25%. However with powders for inhalation or insufflation the proportion used will be within the range of from 0.1-2%.

The foregoing formulations for topical application to the skin may be used for the treatment of inflammatory dermatoses of humans and animals, for example eczema, which are normally responsive to corticosteroid therapy, and also of less responsive conditions such as psoriasis in humans.

The formulations for administration by inhalation or insufflation are intended for administration on a prophylactic basis to humans suffering from allergic and/or inflammatory conditions of the nose, throat or lungs such as asthma and rhinitis, including hay fever. Aerosol formulations are preferably arranged so that each metered dose or "puff" of aerosol contains 20 µg-1000 µg, preferably about 50 µg-100 µg of a compound of the invention. Administration may be several times daily, for example 2, 3, 4 or 8 times, giving for example 1, 2 or 3 doses each time. The overall daily dose with an aerosol will be within the range 100 µg-10 mg preferably, 200 µg-1000 µg. The overall daily dose and the metered dose delivered by capsules and cartridges in an inhaler or insufflator will generally be double those with aerosol formulations.

Topical preparations may be administered by one or more applications per day to the affected area; over skin areas occlusive dressings may often be used with advantage.

For internal administration the new compounds according to the invention may, for example, be formulated in conventional manner for oral, parenteral or rectal administration. For oral administration, syrups, elixirs, powders and granules may be used which may be formulated in conventional manner. Dosage unit forms are however preferred as described below.

Preferred forms of preparation for internal administration are dosage unit forms i.e. tablets and capsules. Such dosage unit forms contain from 0.1 mg to 20 mg preferably from 2.5 to 10 mg of the active steroid.

The compounds according to the invention may in general be given by internal administration in cases where systemic adreno-cortical therapy is indicated.

In general terms preparations for internal administration may contain from 0.05 to 10% of the active ingredient dependent upon the type of preparation involved. The daily dose may vary from 0.1 mg to 60 mg, e.g. 5-30 mg, dependent on the condition being treated, and the duration of treatment desired.

EXAMPLE (A)

| Ointment | |
|---|---|
| Active Ingredient | 0.1% w/w |
| Liquid Paraffin B.P. | 10% w/w |
| White soft paraffin to produce | 100 parts by weight |

Ball-mill the active ingredient with a little of the liquid paraffin until the particle size is reduced to 95% by number below 5µ. Dilute the paste and rinse out the mill with the remaining liquid paraffin, mix and add the suspension to the melted white soft paraffin at 50° C. Stir until cold to give a homogenous ointment.

EXAMPLE (B)

| Cream | % w/w |
|---|---|
| Active ingredient | 0.1 |
| Cetostearyl alcohol | 10.0 |
| Cetamacrogol 1,000 | 2.5 |
| White soft paraffin | 10.0 |
| Liquid paraffin | 10.0 |
| Chlorocresol | 0.1 |
| Sodium acid phosphate | 0.5 |
| Purified water | to 100.0 |

Method of Preparation

The chlorocresol and sodium acid phosphate are dissolved in water at about 70°-75° C. The waxes are melted together at about 65°-70° C. and added with stirring to the aqueous phase when this has cooled to 65°-70° C. The steroid is micronised (particle size as defined in BPC 1973 pg. 911 for Ultra-Fine powder) and dispersed in a portion of the liquid paraffin. The steroid suspension and the remainder of the liquid paraffin are added to the base with stirring at 60° to 65° C. The preparation is cooled with stirring to ambient temperature.

EXAMPLE (C)

| Metered dose aerosol formulation | | | | |
|---|---|---|---|---|
| | per dose | | % w/w | |
| Active ingredient | 0.05 | mg | | 0.059 |
| Fluorotrichloromethane | 25.5 | mg | | 30.0 |
| Dichlorodifluoromethane | to 85.0 | mg | to | 100.0 |

The active ingredient is micronised (particle size as defined in BPC 1973 pg. 911 for Ultra-Fine powder) and dispersed in the fluorotrichloromethane. This suspension is filled into aluminium aerosol containers, the headspace purged with gaseous dichlorodifluoromethane to exclude air, and a metered aerosol valve crimped

EXAMPLE (D)

| Inhalation capsules (100 μg/dose) | | | |
|---|---|---|---|
| | per capsule | | % w/w |
| Active ingredient | 0.1 mg | | 0.4 |
| Lactose | to 25.0 mg | to | 100.0 | into position on the container. Liquid dichlorodifluoromethane is pumped through the metering valve, under pressure, to weight.

The active ingredient is micronised (particle size as defined in BPC 1973 pg. 911 for Ultra-Fine powder) and blended with lactose in the proportions given in the above formula. The steroid lactose blend is filled into hard gelatin capsules to be administered with an inhalation device.

We claim:

1. Compounds of the formula

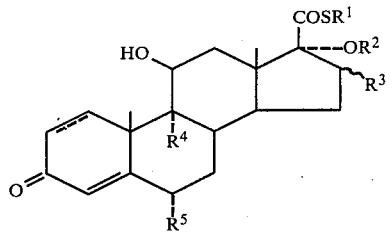

(I)

wherein $R^1$ represents a fluoro-, chloro- or bromomethyl group or a 2'-fluoroethyl group, $R^2$ represents a group $COR^6$ where $R^6$ is a $C_{1-3}$ alkyl group or $OR^2$ and $R^3$ together form a 16α,17α-isopropylidenedioxy group; $R^3$ represents a hydrogen atom, a methyl group (which may be in either the α- or β-configuration) or a methylene group; $R^4$ represents a hydrogen, chlorine or fluorine atom; $R^5$ represents a hydrogen or fluorine atom and the symbol ═══ represents a single or double bond.

2. Compounds as claimed in claim 1 in which $R^1$ is a chloromethyl or fluoromethyl group.

3. Compounds as claimed in claim 1 in which $R^4$ is fluorine.

4. Compounds as claimed in claim 1 which are 1,4-dienes.

5. Compounds as claimed in claim 2 which are 1,4-dienes wherein $R^4$ and $R^5$ are fluorine and $R^3$ is α- or β-methyl or methylene.

6. Compounds as claimed in claim 5 which are 1,4-dienes wherein $R^3$ is α-methyl group.

7. A compound as claimed in claim 1 which is S-chloromethyl 9α-fluoro-11β-hydroxy-16α-methyl-3-oxo-17α-propionyloxyandrosta-1,4-diene-17β-carbothioate.

8. S-chloromethyl 6α, 9α-difluoro-11β-hydroxy-16α-methyl-3-oxo-17α-propionyloxyandrosta-1,4-diene-17β-carbothioate.

9. Pharmaceutical compositions for topical use in antiinflammatory therapy, comprising at least one androstane compound of formula I as defined in claim 1, together with one or more pharmaceutical carriers or excipients.

10. A method of treating inflammation which comprises administering, to a subject suffering from inflammation, an effective amount of a compound of formula I as defined in claim 1.

11. A compound as claimed in claim 1 which is S-chloromethyl 9α-fluoro-11β-hydroxy-16-methylene-3-oxo-17α-propionyloxyandrosta-1,4-diene-17β-carbothioate.

12. A compound as claimed in claim 1 which is S-fluoromethyl 6α, 9α-difluoro-11β-hydroxy-16α, 17α-isopropylidenedioxy-3-oxoandrosta-1,4-diene-17β-carbothioate.

13. A compound as claimed in claim 1 which is S-fluoromethyl 6α, 9α-difluoro-11β-hydroxy-16α-methyl-3-oxo-17α-propionyloxyandrosta-1,4-diene-17β-carbothioate.

14. Compounds as claimed in claim 5 wherein $R^2$ is acetyl or propionyl.

15. A pharmaceutical composition as claimed in claim 9 wherein the active compound is S-chloromethyl 6α, 9α-difluoro-11β-hydroxy-16α-methyl-3-oxo-17α-propionyloxyandrosta-1,4-diene-17β-carbothioate.

16. A pharmaceutical composition as claimed in claim 9 wherein $R^1$ is a chloromethyl or fluoromethyl group, $R^4$ and $R^5$ are fluorine, $R^3$ is α- or β-methyl or methylene and the compound is a 1,4-diene.

17. A method of treating inflammation which comprises administering, to a subject suffering form inflammation, an effective amount of the composition of claim 15.

18. A method of treating inflammation which comprises administering, to a subject suffering from inflammation, an effective amount of the composition of claim 16.

19. A process for the preparation of compounds as claimed in claim 1 in which a compound corresponding to formula I as defined in claim 1 but containing either a free 17β-carbothioic acid group (or salt thereof) or a free 17α-hydroxy group ($R^3$ being a hydrogen atom or a methyl or methylene group), any other reactive groups present optionally being in protected form, is subjected to esterification.

20. A process for the preparation of compounds as claimed in claim 1 in which a compound corresponding to formula I as defined in claim 1 but containing a 17β-substituent of formula —COS(CH$_2$)$_n$Y (wherein Y represents a displaceable substituent and n is 1 or 2) is reacted with a compound serving to replace the group Y by a halogen atom, whereby a compound of formula I as claimed in claim 1 is formed.

21. A process for the preparation of compounds as claimed in claim 1 in which a compound corresponding to formula I as defined in claim 1 but carrying an 11-oxo group is subjected to reduction to form the required 11β-hydroxy androstane.

22. A process for the preparation of compounds as claimed in claim 1 in which a compound corresponding to formula I as defined in claim 1 but carrying a protected 11β-hydroxy group is subjected to deprotection.

23. A process for the preparation of compounds as claimed in claim 1 in which a compound corresponding to formula I as defined in claim 1 but having a 9,11-double bond, and no substituent in the 11-position, is reacted with an N-bromoamide or -imide followed by treatment of the bromohydrin thus obtained with a base to form the corresponding 9,11-epoxide, which epoxide is reacted with hydrogen fluoride or hydrogen chloride whereby a compound of formula I as claimed in claim 1 is formed containing a 9α-fluoro-11 hydroxy or 9-chloro-11β-hydroxy grouping.

24. A process for the preparation of compounds as claimed in claim 1 in which a compound corresponding to formula I as defined in claim 1 but having a 9,11-double bond and no substituent in the 11-position, is reacted with an N-chloro-amide or -imide whereby a compound as claimed in claim 1 is obtained which contains 9α-chloro-11β-hydroxy grouping.

25. A process for the preparation of compounds as claimed in claim 1 in which a compound corresponding to formula I as defined in claim 1 in which === represents a double bond is subjected to partial reduction to produce a corresponding compound in which === represents a single bond.

* * * * *

UNITED STATES PATENT AND TRADEMARK OFFICE
CERTIFICATE OF CORRECTION

PATENT NO. : 4,335,121

DATED : June 15, 1982

INVENTOR(S) : Phillipps et al

It is certified that error appears in the above—identified patent and that said Letters Patent is hereby corrected as shown below:

Column 1, line 9, change "17α" to --17β--;

line 67, change "thalamuspituitary" to --thalamus-pituitary--.

Column 3, line 5, change "anhydried" to --anhydride--.

Column 5, line 8, change "azaaromatic" to --aza-aromatic--;

line 16, change "azaaromatic" to --aza-aromatic--;

line 58, change "in" to --an--.

Column 7, line 16, change "reactive derivatives of formula (III)" to --above-mentioned reactive derivatives corresponding to formula (II)--;

line 21, change "(IV)" to --(III)--;

line 48, change "acyloxy" to --hydroxy--.

Column 9, line 5, insert a hyphen after "17 N,N".

Column 10, line 43, insert a hyphen between "chloroform" and "acetone".

Column 20, line 4, delete "The reaction was diluted with ethyl for 55 mins".

UNITED STATES PATENT AND TRADEMARK OFFICE
CERTIFICATE OF CORRECTION

PATENT NO. : 4,335,121
DATED : June 15, 1982
INVENTOR(S) : Phillipps et al

Page 2 of 2

It is certified that error appears in the above—identified patent and that said Letters Patent is hereby corrected as shown below:

Column 22, line 43, change "the" (second occurrence) to --was--.

Column 26, line 35, change "butryl" to --butyryl--.

Column 29, --Table IV-- to be inserted.

Column 30, --Table IV-- to be inserted.

IN THE CLAIMS:

Claim 17, change "form" to --from--.

Claim 23, change penultimate line to read --is formed containing a 9α-fluoro-11β- hydroxy or 9α- --.

Signed and Sealed this

Eighth Day of March 1983

[SEAL]

Attest:

GERALD J. MOSSINGHOFF

Attesting Officer  Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,335,121

Dated         : June 15, 1982

Inventor(s)   : Gordon H. Phillipps et al

Patent Owner  : Glaxo Group Ltd.

This is to certify that there has been presented to the

COMMISSIONER OF PATENTS AND TRADEMARKS an application under 35 U.S.C. 156 for an extension of the
patent term. Since it appears that the requirements of the law
have been met, this certificate extends the term of the patent
for the period of 1,004 DAYS with all rights pertaining thereto as provided by
35 U.S.C. 156 (b).

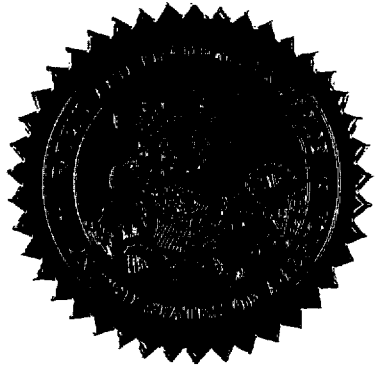

I have caused the seal of the Patent
and Trademark Office to be affixed
this 30th day of December 1991.

Harry F. Manbeck, Jr.
Assistant Secretary and Commissioner
   of Patents and Trademarks